US011376354B2

(12) United States Patent
Nilsson

(10) Patent No.: US 11,376,354 B2
(45) Date of Patent: *Jul. 5, 2022

(54) APPARATUS FOR EXTRACORPOREAL BLOOD TREATMENT

(71) Applicant: GAMBRO LUNDIA AB, Lund (SE)

(72) Inventor: Anders Nilsson, Södra Sandby (SE)

(73) Assignee: Gambro Lundia AB, Lund (SE)

( * ) Notice: Subject to any disclaimer, the term of this patent is extended or adjusted under 35 U.S.C. 154(b) by 470 days.

This patent is subject to a terminal disclaimer.

(21) Appl. No.: 16/463,784

(22) PCT Filed: Oct. 26, 2017

(86) PCT No.: PCT/EP2017/077530
§ 371 (c)(1),
(2) Date: May 23, 2019

(87) PCT Pub. No.: WO2018/095691
PCT Pub. Date: May 31, 2018

(65) Prior Publication Data
US 2019/0374699 A1 Dec. 12, 2019

(30) Foreign Application Priority Data

Nov. 25, 2016 (SE) .................................. 1651543-9

(51) Int. Cl.
*A61M 1/34* (2006.01)
*A61M 1/16* (2006.01)
*A61M 1/36* (2006.01)

(52) U.S. Cl.
CPC ........ *A61M 1/3424* (2014.02); *A61M 1/1601* (2014.02); *A61M 1/1603* (2014.02);
(Continued)

(58) Field of Classification Search
CPC .............. A61M 1/1601; A61M 1/1603; A61M 1/1605; A61M 1/1613; A61M 1/1615;
(Continued)

(56) References Cited

U.S. PATENT DOCUMENTS

| | | |
|---|---|---|
| 4,508,622 A | 4/1985 | Polaschegg et al. |
| 5,567,320 A | 10/1996 | Goux et al. |

(Continued)

FOREIGN PATENT DOCUMENTS

| | | |
|---|---|---|
| CN | 103547300 A | 1/2014 |
| CN | 107666918 A | 2/2018 |

(Continued)

OTHER PUBLICATIONS

Goureau Y., et al. "Evaluation of Plasma Sodium Concentration During Hemodialysis by Computerization of Dialysate Conductivity", vol. 36, No. 3., Jul. 1, 1990; (4 pages).

(Continued)

*Primary Examiner* — John Kim
(74) *Attorney, Agent, or Firm* — K&L Gates LLP

(57) ABSTRACT

An extracorporeal blood treatment apparatus is provided comprising a filtration unit (2) connected to a blood circuit (17) and to a dialysate circuit (32); a control unit (12) is configured for calculating a sodium concentration value for the blood; the estimation of the sodium concentration includes the sub-step of calculating the sodium concentration value as an algebraic sum of a main contribution term based on the isoconductive sodium concentrate and of an offset contribution term based on a concentration of at least a substance in the dialysis fluid chosen in the group including bicarbonate, potassium, acetate, lactate, citrate, magnesium, calcium, sulphate and phosphate.

23 Claims, 1 Drawing Sheet

(52) U.S. Cl.
CPC ........ *A61M 1/1605* (2014.02); *A61M 1/1613* (2014.02); *A61M 1/1615* (2014.02); *A61M 1/1617* (2014.02); *A61M 1/342* (2013.01); *A61M 1/3403* (2014.02); *A61M 1/3406* (2014.02); *A61M 1/3413* (2013.01); *A61M 1/3431* (2014.02); *A61M 1/3434* (2014.02); *A61M 1/3437* (2014.02); *A61M 1/3455* (2013.01); *A61M 1/3462* (2013.01); *A61M 1/361* (2014.02); *A61M 1/3607* (2014.02); *A61M 1/3609* (2014.02); *A61M 1/3612* (2014.02); *A61M 1/3465* (2014.02); *A61M 1/3621* (2013.01)

(58) Field of Classification Search
CPC .. A61M 1/1617; A61M 1/3413; A61M 1/342; A61M 1/3403; A61M 1/3406; A61M 1/3424; A61M 1/3431; A61M 1/3434; A61M 1/3437; A61M 1/3455; A61M 1/3465; A61M 1/3607; A61M 1/3462; A61M 1/3609; A61M 1/3612; A61M 1/361; A61M 1/3621
See application file for complete search history.

(56) References Cited

U.S. PATENT DOCUMENTS

| | | |
|---|---|---|
| 5,744,031 A | 4/1998 | Bene |
| 6,110,384 A | 8/2000 | Goux et al. |
| 6,123,847 A | 9/2000 | Bene |
| 6,126,831 A | 10/2000 | Rainer et al. |
| 6,187,199 B1 | 2/2001 | Rainer |
| 6,860,866 B1 | 3/2005 | Thomas et al. |
| 7,077,819 B1 | 7/2006 | Rainer et al. |
| 8,182,692 B2 | 5/2012 | Gotch |
| 10,828,410 B2 * | 11/2020 | Nilsson ................ G01N 27/04 |
| 2008/0296226 A1 | 12/2008 | Gotch |
| 2010/0168925 A1 | 7/2010 | Hilgers et al. |
| 2012/0018379 A1 | 1/2012 | Gross et al. |
| 2013/0116650 A1 | 5/2013 | Vantard et al. |
| 2013/0274642 A1 | 10/2013 | Orhan et al. |
| 2014/0263064 A1 | 9/2014 | Jones et al. |
| 2015/0343129 A1 | 12/2015 | Surace et al. |
| 2018/0147335 A1 * | 5/2018 | Nilsson ................ A61M 1/3413 |
| 2021/0015984 A1 * | 1/2021 | Nilsson ................ G01R 19/22 |

FOREIGN PATENT DOCUMENTS

| | | |
|---|---|---|
| EP | 0330892 | 9/1989 |
| EP | 547025 | 6/1993 |
| EP | 0578585 | 10/1996 |
| EP | 920877 | 6/1999 |
| EP | 1104682 | 6/2001 |
| EP | 1389475 | 2/2004 |
| EP | 1776971 | 4/2007 |
| EP | 2377563 | 10/2011 |
| EP | 2377563 B1 | 5/2012 |
| EP | 2292284 | 2/2014 |
| EP | 2368582 B1 | 10/2014 |
| WO | 9855166 | 12/1998 |
| WO | 0002604 | 1/2000 |
| WO | 2005044339 | 5/2005 |
| WO | 2005063320 | 7/2005 |
| WO | 2010121805 | 10/2010 |
| WO | 2012127298 | 9/2012 |
| WO | 2012148781 | 11/2012 |
| WO | 2012172398 | 12/2012 |
| WO | 2016026569 | 2/2016 |
| WO | 2016188950 | 12/2016 |
| WO | 2016188951 | 12/2016 |
| WO | 2016188952 | 12/2016 |
| WO | 2017080969 | 5/2017 |
| WO | 2017080970 | 5/2017 |
| WO | 2018095690 | 5/2018 |
| WO | 2018095694 | 5/2018 |

OTHER PUBLICATIONS

International Search Report and Written Opinion for International Application No. PCT/EP2017/077530, dated Feb. 12, 2018; (15 pages).
Swedish Search Report for Swedish Application No. 1651543-9, dated Jul. 3, 2017; (7 pages).
Lauer, et al., "Sodium Fluxes During Hemodialysis", Trans AM Soc Artif Intern Organs (1983), vol. 29, pp. 684-687.
Chinese Search Report dated May 23, 2021, Chinese Application No. 2017800847522.
First Chinese Office Action dated May 28, 2021, Chinese Application No. 2017800847522—18 Pages.

* cited by examiner

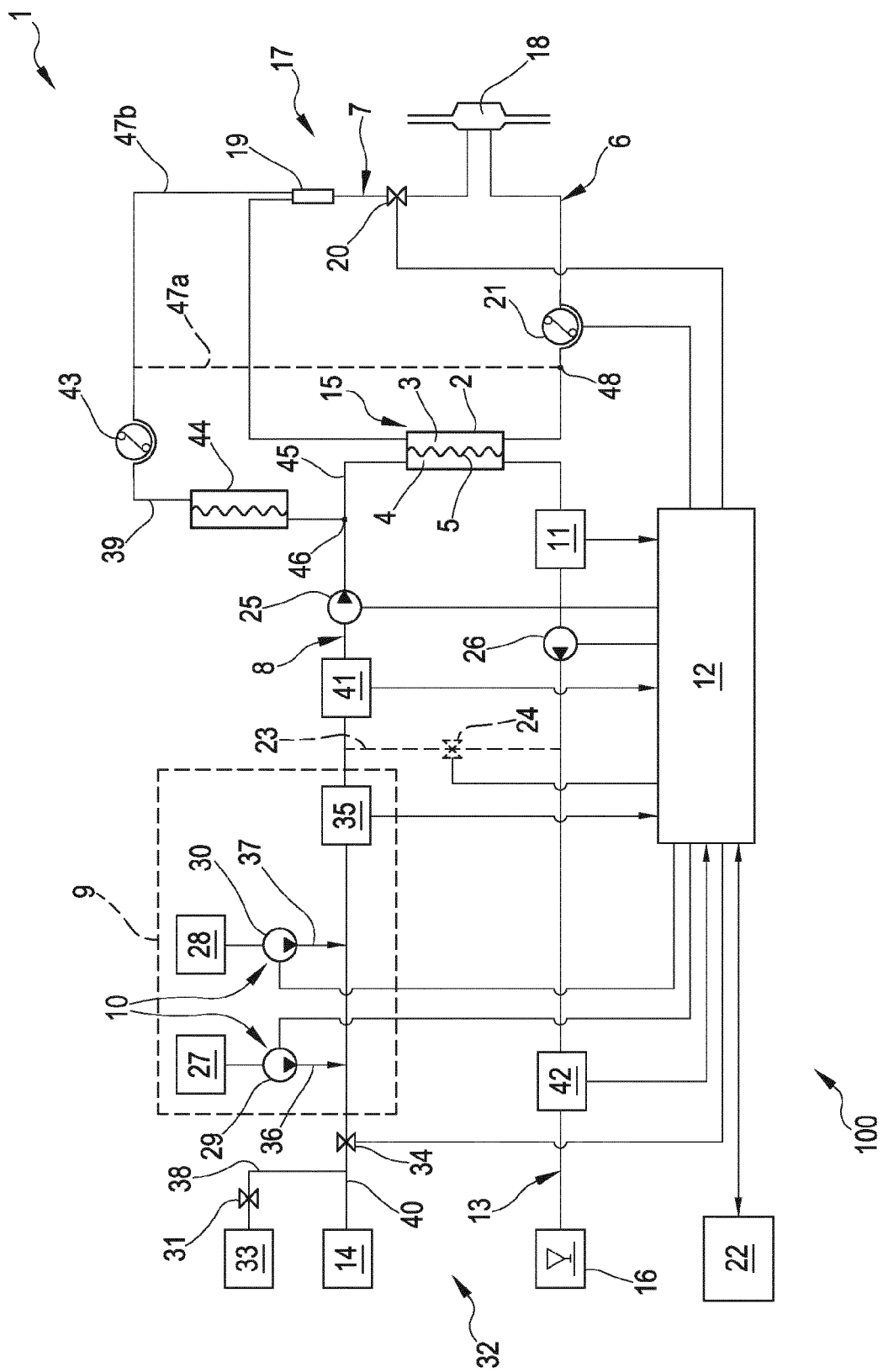

APPARATUS FOR EXTRACORPOREAL BLOOD TREATMENT

TECHNICAL FIELD

The present invention relates to an apparatus for extracorporeal blood treatment and a method for estimating a blood parameter in an extracorporeal blood treatment apparatus.

In particular, the invention may allow determining a blood parameter (e.g. plasma sodium) during a hemodialysis, a hemofiltration, or hemodiafiltration treatment through post-dialyzer conductivity measurements.

BACKGROUND OF THE INVENTION

The kidneys fulfil many functions, including the removal of water, the excretion of catabolites (or waste from the metabolism, for example urea and creatinine), the regulation of the concentration of the electrolytes in the blood (e.g. sodium, potassium, magnesium, calcium, bicarbonates, phosphates, chlorides) and the regulation of the acid/base equilibrium within the body, which is obtained in particular by the removal of weak acids and by the production of ammonium salts.

In individuals who have lost the use of their kidneys, since these excretion and regulation mechanisms no longer work, the body accumulates water and waste from the metabolism and exhibits an excess of electrolytes, as well as, in general, acidosis, the pH of the blood plasma shifting downwards, below 7.35 (the blood pH normally varies within narrow limits of between 7.35 and 7.45).

In order to overcome renal dysfunction, resort is conventionally made to a blood treatment involving extracorporeal circulation through an exchanger having a semipermeable membrane (dialyzer) in which the patient's blood is circulated on one side of the membrane and a dialysis liquid, comprising the main electrolytes of the blood in concentrations close to those in the blood of a healthy subject, is circulated on the other side.

Furthermore, a pressure difference is created between the two compartments of the dialyzer which are delimited by the semipermeable membrane, so that a fraction of the plasma fluid passes by ultrafiltration through the membrane into the compartment containing the dialysis liquid.

The blood treatment which takes place in a dialyzer as regards waste from the metabolism and electrolytes results from two mechanisms of molecular transport through the membrane.

On the one hand, the molecules migrate from the liquid where their concentration is higher to the liquid where their concentration is lower. This is diffusive transport.

On the other hand, certain catabolites and certain electrolytes are entrained by the plasma fluid which filters through the membrane under the effect of the pressure difference created between the two compartments of the exchanger. This is convective transport.

Three of the abovementioned functions of the kidney, namely the removal of water, the excretion of catabolites and the regulation of the electrolytic concentration of the blood, are therefore performed in a conventional blood treatment device by the combination of dialysis and blood filtration (this combination is referred to as hemodialysis).

Some known dialysis machines offer options for both ultrafiltration and sodium profiling with an attempt to improve tolerance for ultrafiltration as dialysis session time became shorter. Indeed reduced dialysis time is associated to an increase in patient intolerance for the consequent higher UF rate.

In simple terms, the UF rate is varied so to favor improved vascular refilling. Moreover, the sodium content of the dialysis fluid is varied during the course of the treatment to directly influence plasma sodium levels. The intent is to control the rate at which sodium leaves the bloodstream into the dialysate.

There can be negative consequences to a high dialysate sodium concentration. Sodium can accumulate in the patient leading to an increased post-dialysis thirst, increased inter-dialytic weight gain and the development of hypertension. Sodium profiling was developed to achieve the benefits of high plasma sodium levels while at the same time avoiding unnecessary high intradialytic sodium uptake by the patient with the associated risk of sodium loading. The idea is to minimize intradialytic side-effects while removing the amount of sodium necessary to avoid sodium overload.

A normal sodium value post dialysis can be reached for hyper- or hyponatremic patients. However, monitoring of the patient's clinical status will indicate if post dialysis normonatremia is indicated. For example, hypernatremic patients often stabilize at a sodium level that is higher than the post dialysis level and may suffer side effects if hyponatremic dialysis is conducted with the intention of lowering their sodium levels.

In the above described situation a need to properly estimate and to continuously know and control the plasma sodium arises.

It is known from document U.S. Pat. No. 5,100,554 to Polaschegg a method for the in-vivo determination of hemodialysis parameters. To carry out hemodialysis with the greatest efficiency and safety, it is necessary to know the dialysis dose which depends on the clearance of the filtration unit. To be able to determine the same in vivo, the invention provides a method in which the electrolyte transfer of the dialysis fluid is measured by means of a conductivity meter at two different predetermined dialysis fluid ion concentrations and both the dialysance and plasma conductivity are determined on the basis thereof.

Document EP547025 to Sternby teaches a method for determining a concentration of sodium in the blood of a patient undergoing a dialysis treatment in an artificial kidney and/or the actual dialysance for sodium of the artificial kidney. The artificial kidney comprises an extracorporeal blood circuit connected to a filtration unit with a semipermeable membrane delimiting a first compartment for the circulation of blood on one side of the membrane and a second compartment for circulating the dialysis fluid; the method includes the steps of circulating successively in the second compartment of the filtration unit a first and a second dialysis liquid having different concentrations of sodium, measuring in the first and second dialysis liquids the conductivity upstream and downstream of the filtration unit, and calculating from the measured conductivity in the first and second dialysis fluids, the conductivity of the blood at the inlet of the filtration unit and/or the actual dialysance of the artificial kidney.

In particular, the conductivity of the blood and the actual dialysance is calculated according to the formula:

$$\kappa_{d\ out} = \kappa_{d\ in} + (\kappa_{b\ in} - \kappa_{d\ in}) \times D/Q_d$$

wherein $\kappa_{d\ in}$=conductivity of the dialysis liquid upstream of the filtration unit;

$\kappa_{d\ out}$=conductivity of the dialysis liquid downstream of the filtration unit;

$\kappa_{b\ in}$=conductivity of the blood upstream of the filtration unit;

D=dialysance of the artificial kidney for conductivity;

$Q_d$=flow rate of the dialysis liquid.

EP658352, EP920877, and EP1108438 describe further improvements of the above described method for plasma conductivity calculation.

The basic principle of the above described monitoring systems is the continuous measurement of the outlet dialysate conductivity when the inlet dialysate conductivity is changed for about 1 mS/cm during two minutes. This measurement can be programmed to take place every e.g. 15, 30, 45 or 60 minutes.

The mathematical outlet conductivity modeling allows the calculation of two dialysis process parameters, namely plasma conductivity and effective ionic dialysance or ionic clearance Plasma conductivity is the reflection of the amount of electrolytes, such as sodium and other physiologically acceptable ions, in the patient. This enables to determine if patients will leave the clinic overloaded with sodium.

Notwithstanding the use of the above identified methods is today largely spread, there are still outstanding problems to give the blood property result a physiological meaning.

Strictly the "plasma conductivity" not only measure an unambiguous blood property but it is strongly influenced by the measurement itself. Generally it is assumed that if the conductivity in fluid entering the filtration unit is equal to the conductivity leaving the filtration unit will represent an unambiguous blood property. However this is an approximation and it is almost impossible to verify correctness of the calculation by taking and measuring samples of the blood. In the past, there have been attempts to statistically connect plasma conductivity to plasma sodium, but the spread in data is large.

SUMMARY

An aim of the present invention is providing an extracorporeal blood treatment apparatus capable to properly estimate a blood parameter in the extracorporeal blood.

In detail it is an aim of the present invention to provide an extracorporeal blood treatment apparatus with a proper tool for estimating a concentration of at least a substance in the blood or a concentration-related parameter of at least a substance in the blood.

A further aim of the invention is to make available an extracorporeal blood treatment apparatus provided with a simple model of the ion transports in the filtration unit that contribute to conductivity change. The mathematical model allows the calculation of the plasma sodium from the conductivity measurements once known or estimated the blood values of some electrolytes.

It is an auxiliary aim of the invention to provide an extracorporeal blood treatment machine configured to automatically perform a proper automatic setting of the dialysis fluid conductivity based on the determined blood parameter.

A further auxiliary aim of the invention is to make available a dialysis apparatus able to provide an automated delivery and control of the dialysis prescription, particularly in order to restore at each dialysis session the proper sodium-water equilibrium to the patient.

It is an object to provide an extracorporeal blood treatment apparatus configured to properly estimate the concentration of at least a substance (e.g. sodium) in the blood or the concentration-related parameter of at least a substance in the blood and to run a renal treatment in any of hemodialysis (HD), hemofiltration (HF) and hemodiafiltration (HDF) treatment modes.

At least one of the above-indicated aims is attained by an apparatus and a corresponding method as in one or more of the appended claims, taken singly or in any combination.

According to a first independent aspect of the invention an extracorporeal blood treatment apparatus is provided including:

a filtration unit (2) having a primary chamber (3) and a secondary chamber (4) separated by a semi-permeable membrane (5);

a blood withdrawal line (6) connected to an inlet of the primary chamber (3), a blood return line (7) connected to an outlet of the primary chamber (3), said blood lines being configured for connection to a patient cardiovascular system;

a dialysis supply line (8) including at least an infusion line (39) connected to said blood circuit, optionally the dialysis supply line (8) comprising an inlet line (45) connected to an inlet of the secondary chamber (4) for circulating a dialysis fluid;

a dialysis effluent line (13) connected to an outlet of the secondary chamber (4);

a control unit (12) configured to run at least a hemofiltration treatment (HF) or a hemodiafiltration treatment (HDF), each of said treatment including an infusion of substitution fluid through said infusion line (39), the control unit being programmed for receiving a value of a first parameter representative of an isoconductive dialysis, the first parameter being chosen in the group including a concentration of at least a substance, a concentration related parameter of at least a substance, a conductivity or a conductivity related parameter, wherein said control unit (12) is configured for:

calculating the value of a second parameter, said second parameter being chosen in a group including a concentration of at least a substance in the blood and a concentration-related parameter of at least a substance in the blood; wherein the step of calculating the value of the second parameter is performed as a function of a main contribution term based on the first parameter and as a function of an offset contribution term based on a concentration of at least a substance in the dialysis fluid chosen in the group including bicarbonate, potassium, acetate, lactate, citrate, magnesium, calcium, sulphate, and phosphate; and optionally, storing said parameter value in a memory (46) connected to the control unit (12).

In a further independent aspect, an apparatus for extracorporeal blood treatment is provided comprising:

a filtration unit (2) having a primary chamber (3) and a secondary chamber (4) separated by a semi-permeable membrane (5);

a blood withdrawal line (6) connected to an inlet of the primary chamber (3), a blood return line (7) connected to an outlet of the primary chamber (3), said blood lines being configured for connection to a patient cardiovascular system;

a dialysis effluent line (13) connected to an outlet of the secondary chamber (4);

a control unit (12) configured to run at least a hemofiltration treatment (HF) or a hemodiafiltration treatment (HDF), each of said treatment including an infusion of substitution fluid through said infusion line (39), the control unit being programmed for receiving a value of a first parameter representative of an isoconductive dialysis, the first parameter being chosen in the group including a concentration of at least a substance, a concentration related parameter of at least a substance, a conductivity or a conductivity related parameter, wherein said control unit (12) is configured for:

calculating the value of a second parameter of the blood, said second parameter being chosen in a group including a concentration of at least a substance in the blood and a concentration-related parameter of at least a substance in the blood; wherein the calculating the parameter value is performed as a function of a main contribution term based on the first parameter and as a function of an offset contribution term based on a concentration of at least a substance in the blood chosen in the group including bicarbonate, potassium, acetate, lactate, citrate, magnesium, calcium, sulphate, and phosphate; and optionally, storing said second parameter value in a memory (46) connected to the control unit (12), in particular the parameter value being the plasma sodium concentration.

In a further independent aspect a method for estimating a blood parameter in an apparatus for extracorporeal blood treatment is provided, the apparatus comprising:

a filtration unit (2) having a primary chamber (3) and a secondary chamber (4) separated by a semi-permeable membrane (5);

a blood withdrawal line (6) connected to an inlet of the primary chamber (3);

a blood return line (7) connected to an outlet of the primary chamber (3), said blood lines being configured for connection to a patient cardiovascular system;

a dialysis supply line (8) including at least an infusion line (39) connected to said blood circuit, optionally connected to an inlet of the secondary chamber (4) for circulating a dialysis fluid;

a dialysis effluent line (13) connected to an outlet of the secondary chamber (4);

a control unit (12) configured to run at least a hemofiltration treatment (HF) or a hemodiafiltration treatment (HDF), each of said treatment including an infusion of substitution fluid through said infusion line (39), the control unit being programmed for receiving a value of a first parameter representative of an isoconductive dialysis, the first parameter being chosen in the group including a concentration of at least a substance, a concentration related parameter of at least a substance, a conductivity or a conductivity related parameter, the method comprising the following steps performed by the control unit:

calculating the value of a second parameter of the blood, said second parameter being chosen in a group including a concentration of at least a substance in the blood and a concentration-related parameter of at least a substance in the blood; wherein the step of calculating the value of the second parameter is performed as a function of a main contribution term based on the first parameter and as a function of an offset contribution term based on a difference, in particular a weighted difference, in concentration of at least a substance in the dialysis fluid and the same substance in the blood plasma, in particular wherein for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid; and storing said second parameter value in a memory (46) connected to the control unit (12).

In a $2^{nd}$ aspect according to anyone of the previous aspects, the control unit is configured to calculate the offset contribution term based on the concentration of two or more substances in the dialysis fluid chosen in the group including bicarbonate, potassium, acetate, lactate, citrate, magnesium, calcium, sulphate, and phosphate, in particular as a function of the concentration of at least three of said substances, optionally as a function of the concentration of bicarbonate, potassium, acetate, and citrate in the dialysis fluid, wherein for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a $3^{rd}$ aspect according to anyone of the previous aspects, the control unit is configured to calculate the offset contribution term as a function of the difference, in particular a weighted difference, in concentration of at least a substance in the dialysis fluid and the same substance in the blood plasma, wherein for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a $4^{th}$ aspect according to anyone of the previous aspects, the control unit is configured to calculate the offset contribution term as a function of the difference, in particular a weighted difference, in concentration of at least a substance in the dialysis fluid and the same substance in the plasma, said substance being chosen in the group including bicarbonate, potassium, acetate, lactate, and citrate, in particular as a function of the difference, in particular a weighted difference, in concentration of at least two of said substances, optionally as a function of the difference, in particular a weighted difference, in concentration of bicarbonate, potassium, and acetate in the dialysis fluid and plasma, even more optionally as a function of the difference, in particular a weighted difference, in concentration of bicarbonate, potassium, citrate, and acetate in the dialysis fluid and plasma, wherein for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a 5$^{th}$ aspect according to anyone of the previous aspects, the value representative of the isoconductive dialysis is chosen in the group including a concentration of at least a substance in the dialysis fluid, a concentration related parameter of at least a substance in the dialysis fluid, a dialysis fluid conductivity, a dialysis fluid conductivity related parameter, a plasma conductivity or a plasma conductivity related parameter, in particular the first parameter is an isoconductive sodium concentration or an isoconductive sodium concentration-related parameter.

In a 6$^{th}$ aspect according to anyone of the previous aspects, the second parameter is the concentration of at least a substance in the blood, said substance being in particular sodium.

In a 7$^{th}$ aspect according to anyone of the previous aspects, the first parameter is the isoconductive sodium concentration and the second parameter is the sodium concentration in the blood.

In a 8$^{th}$ aspect according to anyone of the previous aspects, the main contribution term is dimensionally a concentration of a substance in a fluid.

In a 9$^{th}$ aspect according to the previous aspect, the main contribution term is a concentration value which if used as a dialysis fluid concentration of sodium would run an isoconductive dialysis.

In a 10$^{th}$ aspect according to anyone of the previous aspects, the main contribution term affects the second parameter for at least 80% of the second parameter value, the offset contribution term contributes to the second parameter for less than 20% of the second parameter value.

In a 11$^{th}$ aspect according to anyone of the previous aspects, the sub-step of calculating the second parameter value as a function of the main contribution term and the offset contribution term is a sub-step of calculating an algebraic sum, particularly a weighted algebraic sum, of at least the main contribution term and the offset contribution term and particularly wherein the offset contribution term is dimensionally a concentration of a substance in a fluid.

In a 12$^{th}$ aspect according to anyone of the previous aspects, the main contribution term affects the second parameter for at least 90% of the second parameter value, the offset contribution term contributing to the second parameter for less than 10% of the second parameter value.

In a 13$^{th}$ aspect according to anyone of the previous aspects, the apparatus includes a preparation device (9) for preparing a dialysis fluid connected to said supply line (8) and comprising regulating means (10) for regulating the composition of the dialysis fluid, the regulating means (10) being connected to the control unit (12).

In a 14th aspect according to the previous aspect, the control unit (12) is configured for setting a third parameter value for the dialysis fluid in the dialysis supply line (8) at a set point, said third parameter of the dialysis fluid being at least one chosen in a group including a conductivity of the dialysis fluid, a conductivity-related parameter of the dialysis fluid, a concentration of at least a substance in the dialysis fluid and a concentration-related parameter of at least a substance in the dialysis fluid.

In a 15$^{th}$ aspect according to the previous 13$^{th}$ aspect, the control unit (12) is configured for determining a profile in time for a third parameter value for the dialysis fluid in the dialysis supply line (8), said third parameter of the dialysis fluid being at least one chosen in a group including a conductivity of the dialysis fluid, a conductivity-related parameter of the dialysis fluid, a concentration of at least a substance in the dialysis fluid and a concentration-related parameter of at least a substance in the dialysis fluid; wherein the control unit drives the regulating means (10) for regulating the conductivity or the concentration of at least a substance in the dialysis fluid, the profile in time for the third parameter being based on the second parameter.

In a 16$^{th}$ aspect according to anyone of the previous aspects, the control unit drives regulating means (10) for regulating the conductivity or the concentration of at least a substance in the dialysis fluid.

In a 17$^{th}$ aspect according to the previous four aspects, the control unit setting the third parameter value for the dialysis fluid in the dialysis supply line (8) at the set point which is based on the second parameter.

In a 18$^{th}$ aspect according to the previous aspect, the regulating means (10) regulates the concentration of at least a substance in the dialysis fluid, in particular a ionic substance, such as sodium.

In a 19$^{th}$ aspect according to the previous aspect, the control unit drives the regulating means (10) for regulating the sodium concentration in the dialysis fluid to set the parameter value for the dialysis fluid in the dialysis supply line (8) at the calculated second parameter value.

In a 20$^{th}$ aspect according to anyone of the previous aspects, the control unit is configured to calculate the offset contribution term as a function of the molar conductivities of at least a substance in the dialysis fluid chosen in the group including sodium bicarbonate ($NaHCO_3$), sodium chloride (NaCl), sodium acetate ($NaCH_3COO$), potassium chloride (KCl), sodium lactate ($NaC_3H_5O_3$), and trisodium citrate ($Na_3C_6H_5O_7$), in particular as a function of the molar conductivities of at least two of said substances, in more detail as a function of the molar conductivities of at least three of said substances, optionally as a function of the molar conductivities of at least three substances chosen in the group including sodium bicarbonate ($NaHCO_3$), sodium chloride (NaCl), sodium acetate ($NaCH_3COO$), trisodium citrate ($Na_3C_6H_5O_7$), and potassium chloride (KCl).

In a 21$^{st}$ aspect according to anyone of the previous aspects, the control unit is configured to calculate the offset contribution term as a function of a difference between two molar conductivities.

In a 22$^{nd}$ aspect according to anyone of the previous aspects, the control unit is configured to calculate the offset contribution term as a function of a difference between a first molar conductivity of a substance chosen in the group including sodium bicarbonate ($NaHCO_3$), sodium acetate ($NaCH_3COO$), trisodium citrate ($Na_3C_6H_5O_7$), sodium lactate ($NaC_3H_5O_3$), potassium chloride (KCl), and a molar conductivity of sodium chloride (NaCl).

In a 23$^{rd}$ aspect according to anyone of the previous aspects, the control unit is configured to calculate the offset contribution term as a function of a difference between a molar conductivity of sodium bicarbonate ($NaHCO_3$), and a molar conductivity of sodium chloride (NaCl).

In a 24$^{th}$ aspect according to anyone of the previous aspects, the control unit is configured to calculate the offset contribution term as a function of a difference between a molar conductivity of sodium acetate ($NaCH_3COO$), and a molar conductivity of sodium chloride (NaCl).

In a 25$^{th}$ aspect according to anyone of the previous aspects, the control unit is configured to calculate the offset contribution term as a function of a molar conductivity of potassium chloride (KCl).

In a 26$^{th}$ aspect according to anyone of the previous aspects, the control unit is configured to calculate the offset contribution term as a function of an estimated or measured plasma water concentration of at least a substance chosen in the group including bicarbonate, potassium, acetate, lactate, and citrate, in particular as a function of the estimated or measured plasma water concentration of at least two of said substances, in more detail as a function of the estimated plasma water concentration of at least three of said substances, optionally as a function of the estimated plasma water concentration of bicarbonate, potassium, citrate, and acetate, wherein for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a $27^{th}$ aspect according to the previous aspect, the estimated plasma water concentration of at least a substance chosen in the group including bicarbonate, potassium, citrate, and acetate is the mean pre-dialysis values of the corresponding substance for large patient populations or historical data of the corresponding substance for the individual patient or theoretical values of the corresponding substance or measured values of the corresponding substance.

In a $28^{th}$ aspect according to anyone of the previous aspects $26^{th}$ and $27^{th}$, the estimated plasma water concentration is adjusted by a respective adjusting factor taking account of the Donnan effect.

In a $29^{th}$ aspect according to anyone of the previous aspects, the control unit is configured to calculate the offset contribution term as an algebraic sum of at least two components, a first component being function of the difference, in particular a weighted difference, in concentration of at least a substance in the dialysis fluid and the same substance in the blood plasma, the second component being function of the difference, in particular a weighted difference, in concentration of at least a second substance in the dialysis fluid and the same second substance in the blood plasma, wherein for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a $30^{th}$ aspect according to anyone of the previous aspects, the control unit is configured to calculate the offset contribution term as an algebraic sum of at least three components, a first component being function of the difference, in particular a weighted difference, in concentration of at least a substance in the dialysis fluid and the same substance in the blood plasma, the second component being function of the difference, in particular a weighted difference, in concentration of at least a second substance in the dialysis fluid and the same second substance in the blood plasma, the third component being function of the difference, in particular a weighted difference, in concentration of at least a third substance in the dialysis fluid and the same third substance in the blood plasma, optionally a fourth component being function of the difference, in particular a weighted difference, in concentration of at least a fourth substance in the dialysis fluid and the same fourth substance in the blood plasma, wherein for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a $31^{st}$ aspect according to anyone of the previous aspects, the control unit is configured to calculate the offset contribution term as an algebraic sum of at least two components, a first component being function of a concentration of at least a substance in the dialysis fluid and/or in the blood plasma, a second component being function of a concentration of at least a second substance in the dialysis fluid and/or in the blood plasma, wherein for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a $32^{nd}$ aspect according to anyone of the previous aspects, the control unit is configured to calculate the offset contribution term as an algebraic sum of at least three components, a first component being function of a concentration of at least a substance in the dialysis fluid and/or in the blood plasma, a second component being function of a concentration of at least a second substance in the dialysis fluid and/or in the blood plasma, a third component being function of a concentration of at least a third substance in the dialysis fluid and/or in the blood plasma, optionally a fourth component being function of a concentration of at least a fourth substance in the dialysis fluid and/or in the blood plasma, wherein for HDF pre-dilution treatment and HF pre-dilution treatment, said estimated plasma concentration is a diluted plasma concentration, in particular the diluted plasma concentration being function of the blood flow rate and of the infusion flow rate, optionally the diluted plasma concentration being function of a dialyzable blood water fraction for said substance and the plasma water concentration in blood from patient, in detail the diluted plasma concentration being function of a concentration of said substance in the infused fluid.

In a $33^{rd}$ aspect according to anyone of the previous aspects $29^{th}$ to $32^{nd}$, said substance is an ion chosen in the group including bicarbonate anions ($HCO_3^-$), acetate anions ($CH_3CO^-$), citrate anions ($C_6H_5O_7^{3-}$), and potassium ions ($K^+$).

In a $34^{th}$ aspect according to anyone of the previous aspects, the control unit is configured to calculate the offset contribution term as a function of at least one flow rate, in particular the dialysate flow rate at the outlet of the secondary chamber (4).

In a $35^{th}$ aspect according to anyone of the previous aspects, the control unit is configured to calculate the offset contribution term as a function of at least an efficiency parameter of the filtration unit (2), in particular a clearance of the filtration unit (2), optionally the urea clearance.

In a $36^{th}$ aspect according to anyone of the previous aspects, the control unit is configured to calculate the offset contribution term as a function of at least a ratio between one flow rate, in particular the dialysate flow rate at the outlet of the secondary chamber (4), and an efficiency parameter of the filtration unit (2), in particular a clearance of the filtration unit (2), optionally the urea clearance.

In a 37$^{th}$ aspect according to anyone of the previous aspects, the control unit is configured to calculate the offset contribution term as an algebraic sum of at least two, and particularly three or four or five, components, a component being function of at least a ratio between one flow rate, in particular the dialysate flow rate at the outlet of the secondary chamber (4), and an efficiency parameter of the filtration unit (2), in particular a clearance of the filtration unit (2), optionally the urea clearance.

In a 38$^{th}$ aspect according to anyone of the previous aspects, the control unit (12) is programmed for calculating said first parameter value.

In a 39$^{th}$ aspect according to anyone of the previous aspects, the control unit (12) is programmed for receiving as an external input said first parameter value.

In a 40$^{th}$ aspect according to anyone of the previous aspects, the control unit (12) is programmed for storing in a memory (46) said first parameter value, said first parameter value being not calculated by the control unit.

In a 41$^{st}$ aspect according to anyone of the previous aspects, the offset contribution term has a negative value.

In a 42$^{nd}$ aspect according to anyone of the previous aspects, the offset contribution term is a function of a rest term ($K_{rest}$), said rest term being a conductivity contribution from lesser solutes, in particular said lesser solutes being different from sodium, potassium, bicarbonate, and acetate, optionally said lesser solutes being different from sodium, potassium, citrate, bicarbonate, and acetate.

In a 43$^{rd}$ aspect according to anyone of the previous aspects, the offset contribution term is:

$$c_{di,Na,offset} = -\frac{1}{M_{\kappa,NaCl}} * \left[ (M_{\kappa,NaHCO_3} - M_{\kappa,NaCl}) * (\alpha^{-1} * c_{pw,HCO_3} - c_{d,HCO_3}) + M_{\kappa,KCl} * (\alpha * c_{pw,K} - c_{d,K}) + (M_{\kappa,NaAc} - M_{\kappa,NaCl}) * (\alpha^{-1} * c_{pw,Ac} - c_{d,Ac}) + \frac{Q_{do}}{K_u} * (k_{rest}) \right]$$

wherein:
$c_{di,Na,offset}$ Offset contribution term;
$M_{\kappa,NaHCO_3}$ Molar conductivity of sodium bicarbonate (NaHCO$_3$);
$M_{\kappa,NaCl}$ Molar conductivity of sodium chloride (NaCl);
$M_{\kappa,NaAC}$ Molar conductivity of sodium acetate (NaCH$_3$COO);
$M_{\kappa,KCl}$ Molar conductivity of potassium chloride (KCl);
$c_{d,HCO_3}$ Dialysis fluid concentration of bicarbonate as set by the operator;
$c_{d,K}$ Dialysis fluid concentration of potassium ions (K$^+$) as determined by the used concentrate;
$c_{d,Ac}$ Dialysis fluid concentration of acetate as determined by the used concentrate;
$c_{pw,HCO_3}$ Estimated or measured pre-dialysis concentration of bicarbonate (HCO$_3^-$) in plasma water;
$c_{pw,Ac}$ Estimated or measured pre-dialysis concentration of acetate (CH$_3$COO$^-$) in plasma water;
$c_{pw,K}$ Estimated or measured pre-dialysis concentration of potassium (K$^+$) in plasma water;
α Donnan effect corrective factor;

In a 44$^{th}$ aspect according to anyone of the previous aspects 1$^{st}$ to 42$^{nd}$, the offset contribution term is:

$$c_{di,Na,offset} = -\frac{1}{M_{\kappa,NaCl}} * \left[ (M_{\kappa,NaHCO_3} - M_{\kappa,NaCl}) * (\alpha^{-1} * c_{pw,HCO_3} - c_{d,HCO_3}) + M_{\kappa,KCl} * (\alpha * c_{pw,K} - c_{d,K}) + (M_{\kappa,NaAc} - M_{\kappa,NaCl}) * (\alpha^{-1} * c_{pw,Ac} - c_{d,Ac}) + \frac{K_{b_{Cit}}}{K_u} (M_{\kappa_{Na_3Cit}} - 3M_{\kappa_{NaCl}}) ((0.167\alpha^{-3} + 0.125\alpha^{-2} + 0.706\alpha^{-1}) * c_{pw,Na_3Cit} - c_{d,Na_3Cit}) + + \frac{Q_{do}}{K_u} * (k_{rest}) \right]$$

wherein:
$c_{di,Na,offset}$ Offset contribution term;
$M_{\kappa,NaHCO_3}$ Molar conductivity of sodium bicarbonate (NaHCO$_3$);
$M_{\kappa,NaCl}$ Molar conductivity of sodium chloride (NaCl);
$M_{\kappa,NaAc}$ Molar conductivity of sodium acetate (NaCH$_3$COO);
$M_{\kappa,KCl}$ Molar conductivity of potassium chloride (KCl);
$M_{\kappa,Na_3Cit}$ Molar conductivity of trisodium citrate (Na$_3$C$_6$H$_5$O$_7$);
$\kappa_{rest1}$ Conductivity contribution from lesser solutes;
$c_{d,HCO_3}$ Dialysis fluid concentration of bicarbonate as set by the operator;
$c_{d,K}$ Dialysis fluid concentration of potassium ions (K$^+$) as determined by the used concentrate;
$c_{d,Ac}$ Dialysis fluid concentration of acetate as determined by the used concentrate;
$c_{d,Na_3Cit}$ Dialysis fluid concentration of total citrate as determined by the used concentrate;
$c_{pw,HCO_3}$ Estimated or measured pre-dialysis concentration of bicarbonate (HCO$_3$) in plasma water;
$c_{pw,Ac}$ Estimated or measured pre-dialysis concentration of acetate (CH$_3$COO$^-$) in plasma water;
$c_{pw,K}$ Estimated or measured pre-dialysis concentration of potassium (K$^+$) in plasma water;
$c_{pw,Na_3Cit}$ Estimated or measured pre-dialysis concentration of total citrate in plasma water;
$Q_{do}$ Dialysate flow rate at filtration unit outlet;
$K_u$ Filtration unit clearance for urea;
$K_{b_{Cit}}$ Filtration unit clearance for citrate;
α Donnan effect corrective factor;

In a 45$^{th}$ aspect according to anyone of the previous aspects 1$^{st}$ to 42$^{nd}$, in HDF pre-dilution and HF pre-dilution treatment mode, the offset contribution term is:

$$c_{di,Na,offset} = -\frac{1}{M_{\kappa,NaCl}} \cdot \left[ (M_{\kappa,NaHCO_3} - M_{\kappa,NaCl}) \cdot \left( \frac{1}{\alpha_{bi}} \cdot \frac{Q_b \cdot f_{HCO_3} \cdot c_{pw,art_{HCO_3}} + Q_{inf} \cdot c_{d_{HCO_3}}}{Q_b \cdot f_{HCO_3} + Q_{inf}} - c_{d,HCO_3} \right) + M_{\kappa,KCl} \cdot \left( \alpha_{bi} \cdot \frac{Q_b \cdot f_K \cdot c_{pw,art_K} + Q_{inf} \cdot c_{d_K}}{Q_b \cdot f_K + Q_{inf}} - c_{d,K} \right) + (M_{\kappa,NaAc} - M_{\kappa,NaCl}) \cdot \left( \frac{1}{\alpha_{bi}} \cdot \frac{Q_b \cdot f_{Ac} \cdot c_{pw,art_{Ac}} + Q_{inf} \cdot c_{d_{Ac}}}{Q_b \cdot f_{Ac} + Q_{inf}} - c_{d,Ac} \right) + \frac{K_{b_{Cit}}}{K_u} \cdot (M_{\kappa,Na_cCit} - 3M_{\kappa,NaCl}) \cdot (0.167\alpha_{bi}^{-3} + 0.125\alpha_{bi}^{-2} + 0.706\alpha_{bi}^{-1}) \cdot \frac{Q_b \cdot f_{Cit} \cdot c_{pw,art_{Na_3Cit}} + Q_{inf} \cdot c_{d_{Na_3Cit}}}{Q_b \cdot f_{Na_3Cit} + Q_{inf}} - c_{d,Na_3Cit} \right) + \frac{Q_{do}}{K_u} * (k_{rest}) \right]$$

wherein, in HF treatment mode, the clearance being equal to the dialyzer outlet flow, i.e. $K_u = Q_{do}$;

$$\frac{Q_b \cdot f_{HCO_3} \cdot c_{pw,art_{HCO_3}} + Q_{inf} \cdot c_{d_{HCO_3}}}{Q_b \cdot f_{HCO_3} + Q_{inf}}$$

is a diluted plasma water concentration of bicarbonate in blood entering the filtration unit;

$$\frac{Q_b \cdot f_{Ac} \cdot c_{pw,art_{Ac}} + Q_{inf} \cdot c_{d_{Ac}}}{Q_b \cdot f_{Ac} + Q_{inf}}$$

is a diluted plasma water concentration of acetate in blood entering the filtration unit;

$$\frac{Q_b \cdot f_K \cdot c_{pw,art_K} + Q_{inf} \cdot c_{d_K}}{Q_b \cdot f_K + Q_{inf}}$$

is a diluted plasma water concentration of potassium in blood entering the filtration unit;

$$\frac{Q_b \cdot f_{Cit} \cdot c_{pw,art_{Na_3Cit}} + Q_{inf} \cdot c_{d_{Na_3Cit}}}{Q_b \cdot f_{Na_3Cit} + Q_{inf}}$$

is a diluted plasma water concentration of citrate in blood entering the filtration unit;

$c_{di,Na,offset}$ Offset contribution term;

$M_{\kappa,NaHCO_3}$ Molar conductivity of sodium bicarbonate (NaHCO$_3$);

$M_{\kappa,NaCl}$ Molar conductivity of sodium chloride (NaCl);

$M_{\kappa,NaAc}$ Molar conductivity of sodium acetate (NaCH$_3$COO);

$M_{\kappa,KCl}$ Molar conductivity of potassium chloride (KCl);

$c_{d,HCO_3}$ Dialysis fluid concentration of bicarbonate as set by the operator;

$c_{d,K}$ Dialysis fluid concentration of potassium ions (K$^+$) as determined by the used concentrate;

$c_{d,Ac}$ Dialysis fluid concentration of acetate as determined by the used concentrate;

$c_{d,Na_3Cit}$ Dialysis fluid concentration of total citrate as determined by the used concentrate;

$K_{b_{Cit}}$ Dialysate flow rate at filtration unit outlet;

$K_u$ Filtration unit clearance for urea;

$\alpha_{bi}$ Donnan corrective factor in HF/DF pre-dilution mode;

In a 46$^{th}$ aspect according to anyone of the previous aspects, the first parameter is a concentration of at least a substance in the dialysis fluid, said substance being in particular sodium.

In a 47$^{th}$ aspect according to anyone of the previous aspects, the first parameter is an isoconductive substance concentration.

In a 48$^{th}$ aspect according to anyone of the previous aspects, the first parameter is the plasma conductivity or the dialysis fluid conductivity in isoconductive dialysis.

In a 49$^{th}$ aspect according to anyone of the previous aspects, the first parameter is the plasma conductivity related parameter, said plasma conductivity related parameter being the dialysis fluid conductivity in isoconductive dialysis.

In a 50$^{th}$ aspect according to anyone of the previous aspects, the first parameter is the isoconductive sodium concentration related parameter, in particular the plasma conductivity or the dialysis fluid conductivity in isoconductive dialysis.

In a 51$^{st}$ aspect according to anyone of the previous aspects, the first parameter is the isoconductive sodium concentration related parameter, in particular the dialysis fluid conductivity in isoconductive dialysis, and the second parameter is the sodium concentration in the blood.

In a 52$^{nd}$ aspect according to anyone of the previous aspects, immediately after calculating an initial sodium concentration, the control unit is configured to drive the regulating means (10) to change the composition of the dialysis fluid and to set the dialysis fluid sodium to a substantially isoconductive sodium concentration.

In a 53$^{rd}$ aspect according to the previous aspect, after setting the dialysis fluid sodium to a substantially isoconductive sodium concentration, the control unit is configured to execute a second calculating step, based on a second determined initial conductivity of the dialysate and on a second corresponding conductivity of the dialysis fluid in the dialysis supply line (8), of a second estimate of the initial sodium concentration, said calculating the second estimate being performed maintaining the dialysis fluid conductivity substantially constant by an isoconductive sodium concentration setting.

In a 54$^{th}$ aspect according to anyone of the previous aspects, after calculating the second estimate of the isoconductive sodium concentration, the control unit is configured to drive the regulating means (10) to change the composition of the dialysis fluid and to set the dialysis fluid sodium concentration substantially equal to said second estimate.

In a 55$^{th}$ aspect according to anyone of the previous aspects, the control unit (12) is configured to determine the conductivity of the dialysis fluid both upstream and downstream of said filtration unit (2) for at least two successively prepared dialysates with different conductivities, particularly deriving from different concentrations of sodium.

In a 56$^{th}$ aspect according to anyone of the previous aspects, the control unit (12) is configured to store in a memory instruction for configuring the apparatus to run a HD, or a HDF, or HF treatment.

In a 57$^{th}$ aspect according to anyone of the previous aspects, the control unit (12) is configured to use a diluted plasma concentration in calculating the second parameter of the blood.

In a 58$^{th}$ aspect according to the previous aspect, the diluted plasma concentration is function of an infusion fluid flow rate, the infusion fluid being infused in the blood circuit upstream the filtration unit along a blood circulation direction.

Further characteristics and advantages of the present invention will better emerge from the detailed description that follows of at least an embodiment of the invention, illustrated by way of non-limiting example in the accompanying drawings.

BRIEF DESCRIPTION OF THE DRAWINGS

The description will now follow, with reference to the appended FIGURE provided by way of non-limiting example, in which:

FIG. 1 schematically represents an extracorporeal blood treatment apparatus made according to an illustrating embodiment.

DETAILED DESCRIPTION

FIG. 1 illustrates an extracorporeal blood treatment apparatus 1 in an embodiment of the invention.

An example of a hydraulic circuit 100 is schematically illustrated, but it is to be noted that the specific structure of the hydraulic circuit 100 is not relevant for the purposes of the present invention and therefore other and different circuits to those specifically shown in FIG. 1 might be used in consequence of the functional and design needs of each single medical apparatus.

The hydraulic circuit 100 exhibits a dialysis fluid circuit 32 presenting at least one dialysis supply line 8. Depending on the specific apparatus treatment mode, the dialysis supply line 8 may or, may not, assume different hydraulic circuit line configurations.

In a hemodialysis (HD) treatment mode, the supply line 8 is destined to transport a dialysis fluid from at least one source 14 towards a treatment station 15 where one or more filtration units 2, or dialyzers, operate. Dialysis fluid and blood exchange through the semipermeable membrane in the filtration unit 15 mainly by diffusion process.

In a hemofiltration (HF) treatment mode, the supply line 8 comprises an infusion line 39, which is destined to transport an infusion fluid from at least one source 14 to the blood circuit. The infusion line 39 may include an ultrafilter 44 to additionally filter the received fluid upstream the injection point into the blood circuit. The removal of waste products from the blood is achieved by using large amounts of ultrafiltration with simultaneous reinfusion of sterile replacement fluid in the blood circuit.

In a hemodiafiltration (HDF) treatment mode, the supply line 8 is destined to transport the dialysis fluid from the source 14 towards the treatment station 15 and also comprises the infusion line 39 to transport the infusion fluid from the source 14 to the blood circuit 17. HDF is a combination of hemodialysis and hemofiltration.

In general, though not essential, the source 14 for the supply line 8 and the infusion line 39 is the same (i.e. a dialysis fluid preparation devices 9). Of course, different sources may be used.

Additionally, the supply line 8 normally branches into the infusion line 39, infusing fluid in the blood circuit 17, and into an inlet line 45 directing the fluid to the treatment station 15. Referring to FIG. 1, a branch point is indicated with reference numeral 46.

Notwithstanding the fact that different hydraulic circuits 100 may be used to deliver HF, HD and HDF treatments having exclusively the relevant lines for the specific treatment (e.g. no infusion line 39 for HD, no inlet line 45 for HF), generally the hydraulic circuit 100 is of the kind shown in FIG. 1 and includes both infusion line 39 and inlet line 45, the apparatus control unit 12 may then control the passage of fluid trough said lines, depending on the selected treatment, by means e.g. proper valves or clamps.

The dialysis fluid circuit 32 further comprises at least one dialysis effluent line 13, destined for the transport of a dialysate liquid (spent dialysate and liquid ultrafiltered from the blood through a semipermeable membrane 5) from the treatment station 15 towards an evacuation zone, schematically denoted by 16 in FIG. 1.

The hydraulic circuit cooperates with a blood circuit 17, also schematically represented in FIG. 1 in its basic component parts. The specific structure of the blood circuit is also not fundamental, with reference to the present invention. Thus, with reference to FIG. 1, a brief description of a possible embodiment of a blood circuit is made, which is however provided purely by way of non-limiting example.

The blood circuit 17 of FIG. 1 comprises a blood withdrawal line 6 designed to remove blood from a vascular access 18 and a blood return line 7 designed to return the treated blood to the vascular access 18.

The blood circuit 17 of FIG. 1 further comprises a primary chamber 3, or blood chamber, of the blood filtration unit 2, the secondary chamber 4 of which is connected to the hydraulic circuit 100.

In greater detail, the blood withdrawal line 6 is connected at the inlet of the primary chamber 3, while the blood return line 7 is connected at the outlet of the primary chamber 3.

In turn, the dialysis supply line 8 is connected at the inlet of the secondary chamber 4, while the dialysis effluent line 13 is connected at the outlet of the secondary chamber 4.

The filtration unit 2, for example a dialyzer or a plasma filter or a hemofilter or a hemodiafilter, comprises, as mentioned, the two chambers 3 and 4 which are separated by a semipermeable membrane 5, for example of the hollow-fibre type or plate type.

The blood circuit 17 may also comprise one or more air separators 19: in the example of FIG. 1 a separator 19 is included at the blood return line 7, upstream of a safety valve 20.

Of course other air separators may be present in the blood circuit, such as positioned along the blood withdrawal line 6.

The safety valve 20 may be activated to close the blood return line 7 when, for example, for security reasons the blood return to the vascular access 18 has to be halted.

The extracorporeal blood treatment apparatus 1 may also comprise one or more blood pumps 21, for example positive displacement pumps such as peristaltic pumps; in the example of FIG. 1, a blood pump 21 is included on the blood withdrawal line 6.

The apparatus of above-described embodiment may also comprise a user interface 22 (e.g. a graphic user interface or GUI) and a control unit 12, i.e. a programmed/programmable control unit, connected to the user interface.

The control unit 12 may, for example, comprise one or more digital microprocessor units or one or more analog units or other combinations of analog units and digital units. Relating by way of example to a microprocessor unit, once the unit has performed a special program (for example a program coming from outside or directly integrated on the microprocessor card), the unit is programmed, defining a plurality of functional blocks which constitute means each designed to perform respective operations as better described in the following description.

In combination with one or more of the above characteristics, the medical apparatus may also comprise a closing device operating, for example, in the blood circuit 17 and/or in the dialysis fluid circuit 32 and commandable between one first operating condition, in which the closing device allows a liquid to flow towards the filtration unit 2, and a second operative position, in which the closing device blocks the passage of liquid towards the filtration unit 2.

In this case, the control unit 12 may be connected to the closing device and programmed to drive the closing device to pass from the first to the second operative condition, should an alarm condition have been detected.

In FIG. 1 the closing device includes the safety valve 20 (e.g. a solenoid valve) controlled by the unit 12 as described above. Obviously a valve of another nature, either an occlusive pump or a further member configured to selectively prevent and enable fluid passage may be used.

Alternatively or additionally to the safety valve 20, the closing device may also comprise a bypass line 23 which connects the dialysis fluid supply line 8 and the dialysate effluent line 13 bypassing the dialyzer, and one or more fluid check members 24 connected to the control unit 12 for selectively opening and closing the bypass line 23. The components (bypass line 23 and fluid check members 24), which may be alternative or additional to the presence of the safety valve 20 are represented by a broken line in FIG. 1.

The check members 24 on command of the control unit close the fluid passage towards the treatment zone and connect the source 14 directly with the dialysis effluent line 13 through the bypass line 23.

Again with the aim of controlling the fluid passage towards the filtration unit 2, a dialysis fluid pump 25 and a dialysate pump 26 may be included, located respectively on the dialysis fluid supply line 8 and on the dialysate effluent line 13 and also operatively connected to the control unit 12.

The apparatus also comprises a dialysis fluid preparation device 9 which may be of any known type, for example including one or more concentrate sources 27, 28 and respective concentrate pumps 29, 30 for the delivery, as well as at least a conductivity sensor 35.

Of course other kinds of dialysis fluid preparation devices 9 might be equivalently used, having a single or further concentrate sources and/or a single or more pumps.

Since the dialysis apparatus may comprise various liquid sources 14 (for example one or more water sources, one or more concentrate sources 27, 28, one or more sources 33 of disinfectant liquids) connected to the dialysis supply line 8 with respective delivery lines 36, 37 and 38, the apparatus may exhibit, at each delivery line, a respective check member (not all are shown) and, for example, comprising a valve member 31 and 34 and/or an occlusive pump.

The preparation device 9 may be any known system configured for on-line preparing dialysis fluid from water and concentrates.

The dialysis supply line 8 fluidly connects the preparation device 9 for preparing dialysis fluid to the filtration unit 2 and/or to the blood circuit 17. The preparation device 9 may be, for example, the one described in the U.S. Pat. No. 6,123,847 the content of which is herein incorporated by reference.

As shown, the dialysis supply line 8 connects the preparation device 9 for preparing dialysis fluid to the filtration unit 2 and comprises a main line 40 whose upstream end is intended to be connected to a source 14 of running water.

Delivery line/s 36/37 is/are connected to this main line 40, the free end of which delivery line/s is/are intended to be in fluid communication (for example immersed) in a container/s 27, 28 for a concentrated saline solution each containing sodium chloride and/or calcium chloride and/or magnesium chloride and/or potassium chloride.

Concentrate pump/s 29, 30 is/are arranged in the delivery line/s 36/37 in order to allow the metered mixing of water and concentrated solution in the main line 40. The concentrate pump/s 29, 30 is/are driven on the basis of the comparison between 1) a target conductivity value for the mixture of liquids formed where the main line 40 joins the delivery line/s 36/37, and 2) the value of the conductivity of this mixture measured by means of a conductivity sensor 35 arranged in the main line 40 immediately downstream of the junction between the main line 40 and the delivery line/s 36/37.

Therefore, as mentioned, the dialysis fluid may contain, for example, ions of sodium, calcium, magnesium, and potassium and the preparation device 9 may be configured to prepare the dialysis fluid on the basis of a comparison between a target conductivity value and an actual conductivity value of the dialysis fluid measured by the conductivity sensor 35 of the device 9.

The preparation device 9 comprises regulating means 10, of a known type (i.e. concentrate pump/s 29, 30), which is configured to regulate the concentration of a specific substance, in particular an ionic substance, in the dialysis liquid. Generally it is advantageous to control the sodium concentration of the dialysis fluid.

The dialysis supply line 8 forms an extension of the main line 40 of the preparation device 9 for preparing dialysis fluid. Arranged in this dialysis supply line, in the direction in which the liquid circulates, there are the first flow meter 41 and the dialysis fluid pump 25.

The supply line 8 branches (at branch point 46) into the infusion line 39, which, in the example of FIG. 1, is shown directly connected to the blood return line 7, in particular to the air separator 19 (solid line) via post-infusion tract 47b.

Alternatively, the infusion line 39 may infuse infusion fluid in the blood withdrawal line 6 via pre-infusion tract 47a, in particular downstream the blood pump 21 (dotted line) at pre-infusion point 48.

It is also in the scope of the present description an embodiment including an infusion line 39 branching into a pre-infusion branch 47a and in a post-infusion branch 47b directing infusion fluid, respectively, in the blood withdrawal line 6 and in the blood return line 7.

One or more infusion pumps 43 may be used to pump the desired flow of infusion fluid into the blood circuit. The infusion pump 43 may be a positive displacement pump (e.g. a peristaltic pump as shown) or any other pump adapted to displace infusion fluid (e.g. a volumetric pump).

The dialysis effluent line 13 may be provided with a dialysate pump 26 and a second flow meter 42. The first and second flow meters 41, 42 may be used to control (in a known manner) the fluid balance of a patient connected to the blood circuit 17 during a dialysis session.

A sensor 11 is provided on the dialysis effluent line 13, immediately downstream the filtration unit 2, to measure a parameter value of the dialysate in the dialysate effluent line.

In detail, the parameter of the dialysate, which is measured by the sensor 11 is at least one chosen in the group consisting of conductivity of the dialysate, a conductivity-related parameter of the dialysate, concentration of at least a substance in the dialysate and a concentration-related parameter of at least a substance in the dialysate.

In detail the sensor 11 is a conductivity sensor, which is connected to the dialysis effluent line 13, and is configured to detect conductivity values of the dialysate downstream of the filtration unit 2.

Alternatively (or in combination) sensor 11 may include a concentration sensor configured for measuring the concentration of at least one substance in the dialysate, such as sodium concentration.

Correspondingly, sensor 35 on the dialysis fluid supply line may be not a conductivity sensor and, differently, may include a concentration sensor configured for measuring the concentration of at least one substance in the dialysis fluid, such as sodium concentration.

The control unit 12 of the dialysis apparatus represented in FIG. 1 may be connected to a (graphic) user interface 22 through which it may receive instructions, for example target values, such as blood flow rate $Q_b$, dialysis fluid flow rate $Q_{di}$, infusion liquid flow rate $Q_{inf}$ (pre-infusion and/or post-infusion), patient weight loss WL. The control unit 12 furthermore may receive detected values by the sensors of the apparatus, such as the aforementioned flow meters 41, 42, the (e.g. conductivity) sensor 35 of the preparation device 9 and the (e.g. conductivity) sensor 11 in the dialysis effluent line 13. On the basis of the instructions received and the operating modes and algorithms which have been programmed, the control unit 12 drives the actuators of the apparatus, such as the blood pump 21, the aforementioned dialysis fluid and dialysate pumps 25, 26, and the preparation device 9, and the infusion pump 43.

As already mentioned, the described embodiments are intended to be non-limiting examples. In particular the circuits of FIG. 1 should not be interpreted as defining or limiting, as an apparatus such as in the invention may comprise other additional or alternative components to those described.

For example an ultrafiltration line may be included, with at least one respective pump connected to the dialysis effluent line 13.

The blood circuit of FIG. 1 is intended for double needle treatments; however, this is a non-limiting example of the blood set.

Indeed, the apparatus may be configured to perform single needle treatments, i.e. the patient is connected to the extracorporeal blood circuit by way of a single needle and the extracorporeal line from the patient is then split into a withdrawal line and a return line, using, for example, an 'Y' connector. During single needle treatment, a blood withdrawal phase removing blood from patient is alternated to a blood return phase in which blood is restituted to the patient.

Furthermore one or more devices for measuring specific substance concentrations might be implemented either (or both) in the dialysis fluid side or (and) in the blood side of the hydraulic circuit. Concentration of calcium, potassium, magnesium, bicarbonate, and/or sodium might be desired to be known.

Finally, the above-cited one or more pumps and all the other necessary temperature, pressure, and concentration sensors may operate either on the dialysis supply line 8 and/or on the dialysis effluent line 13, in order to adequately monitor the preparation and movement of the liquid in the hydraulic circuit.

Given the above description of a possible embodiment of extracorporeal blood treatment apparatus, thereafter the specific working of the apparatus and the algorithm programming the control unit are described.

Definitions

We define the "dialysis fluid" as the fluid prepared and, when appropriate based on the selected treatment, introduced to the second chamber (4) of the filtration unit (2)—e.g. HD and HDF—, the dialyzer. The dialysis fluid may also be denoted "fresh dialysis fluid".

We define the "dialysate" as the fluid from the outlet from the second chamber (4) of the filtration unit (2), the dialyzer. Dialysate is the spent dialysis fluid, comprising the uremic toxins removed from the blood.

We define "infusion fluid" as the fluid prepared and infused in the blood circuit (17), either in the blood withdrawal line (6) or in the blood return line (7) or in both blood lines (6, 7).

We define 'isoconductive dialysis', as a dialysis treatment where the conductivity of the dialysis fluid does not change pre- to post-filtration unit (2), $\kappa_{di} = \kappa_{do}$.

We define 'plasma conductivity' as the conductivity of the dialysis fluid in an isoconductive dialysis.

We define 'hemodialysis treatment mode' (HD) a dialysis treatment with fresh dialysis fluid is directed to the filtration unit 2 and no substitution fluid is infused in the blood circuit.

We define 'hemofiltration treatment mode' (HF) a treatment with substitution fluid directed into the blood circuit 17 and no fresh dialysis fluid is directed to the filtration unit 2.

We define 'hemofiltration treatment mode' in post-dilution (HF post-dilution) a treatment with substitution fluid directed into the blood circuit 17 downstream the filtration unit (no substitution fluid is directed in the blood circuit upstream the filtration unit).

We define 'hemofiltration treatment mode' in pre-dilution (HF pre-dilution) a treatment with substitution fluid directed into the blood circuit 17 upstream the filtration unit (no substitution fluid is directed in the blood circuit downstream the filtration unit).

We define 'hemodiafiltration treatment mode' (HDF) a treatment with both substitution fluid directed into the blood circuit 17 and fresh dialysis fluid directed to the filtration unit 2.

We define 'hemodiafiltration treatment mode' in post-dilution (HDF post-dilution) a treatment with both substitution fluid is directed into the blood circuit 17 downstream the filtration unit and fresh dialysis fluid directed to the filtration unit 2 (no substitution fluid is directed in the blood circuit upstream the filtration unit).

We define 'hemodiafiltration treatment mode' in pre-dilution (HDF pre-dilution) a treatment with both substitution fluid is directed into the blood circuit 17 upstream the filtration unit and fresh dialysis fluid directed to the filtration unit 2 (no substitution fluid is directed in the blood circuit downstream the filtration unit).

We define 'isoconductive substance concentration' as the substance concentration in the dialysis fluid in an isoconductive dialysis.

We define 'isoconductive sodium concentration' as the sodium concentration of the dialysis fluid in an isoconductive dialysis.

In this application the term "citrate", and also the term "Cit", means that the component is in form of a salt of citric acid, such as sodium, magnesium, calcium, or potassium salt thereof. The citric acid (denoted $C_6H_8O_7$) is deprotonated stepwise, therefore the "citrate" include all the different forms, citrate (denoted $C_6H_5O_7^{3-}$), hydrogen citrate (denoted $C_6H_6O_7^{2-}$), and dihydrogen citrate (denoted $C_6H_7O_7^{-}$).

The term "citrate" or "total citrate" means that the total amount of citric acid and any salts thereof, such as its sodium, magnesium, calcium, or potassium salt thereof.

In other terms, "total citrate" is the sum of free citrate ions and citrate containing complexes and ion pairs.

Glossary

The following terms are consistently used throughout the equations provided in the following description of the detailed working of the extracorporeal blood treatment apparatus.

| | | |
|---|---|---|
| $c_{di,Na,offset}$ | Offset contribution term; | mmol/L |
| $M_{\kappa,NaHCO_3}$ | Molar conductivity of sodium bicarbonate ($NaHCO_3$); | L · mS/ mmol · cm |
| $M_{\kappa,NaCl}$ | Molar conductivity of sodium chloride (NaCl); | L · mS/ mmol · cm |
| $M_{\kappa,NaAc}$ | Molar conductivity of sodium acetate ($NaCH_3COO$); | L · mS/ mmol · cm |

| | | |
|---|---|---|
| $M_{\kappa,KCl}$ | Molar conductivity of potassium chloride (KCl); | L · mS/ mmol · cm |
| $M_{\kappa,Na3}Cit$ | Molar conductivity of trisodium citrate ($Na_3C_6H_5O_7$); | L · mS/ mmol · cm |
| $Q_{inf}$ | Dialysis fluid infusion flow rate, e.g. dialysis fluid directly infused in the blood circuit; | mL/min |
| $Q_{di}$ | Dialysis fluid flow rate at filtration unit inlet; | mL/min |
| $Q_d$ | Total dialysis fluid flow rate; | mL/min |
| $Q_{do}$ | Dialysate flow rate at filtration unit outlet (i.e., Qdi + Quf); | mL/min |
| $Q_{wl}$ | Weight loss rate; | mL/min |
| $Q_u$ | Total ultrafiltration flow rate; | mL/min |
| $Q_{bset}$ | Set blood flow rate at filtration unit inlet; | mL/min |
| $Q_b$ | Real blood flow rate at filtration unit inlet (set blood flow compensated for arterial pressure); | mL/min |
| $Q_{bwi}$ | Dialyzer inlet blood water flow rate; | mL/min |
| $Q_{bwo}$ | Dialyzer outlet blood water flow rate; | mL/min |
| $\kappa_{rest1}$ | Conductivity contribution from lesser solutes; | mS/cm |
| $c_{d,HCO3}$ | Dialysis fluid concentration of bicarbonate as set by the operator; | mmol/L |
| $c_{d,K}$ | Dialysis fluid concentration of potassium ions ($K^+$) as determined by the used concentrate; | mmol/L |
| $c_{d,Ac}$ | Dialysis fluid concentration of acetate as determined by the used concentrate; | mmol/L |
| $c_{d,Na3}Cit$ | Dialysis fluid concentration of total citrate as determined by the used concentrate; | mmol/L |
| $c_{pw,Na}$ | Concentration of sodium ($Na^+$) in plasma water; | mmol/L |
| $c_{pw}$ | Plasma water concentration; | mmol/L |
| $c_{pw,bi}$ | Plasma water concentration in blood entering the filtration unit; | mmol/L |
| $c_{pw,Art}$ | Plasma water concentration in blood from patient; | mmol/L |
| $c_{pw,Ac}$ | Estimated or measured pre-dialysis concentration of acetate ($CH_3COO^-$) in plasma water; | mmol/L |
| $c_{pw,K}$ | Estimated or measured pre-dialysis concentration of potassium ($K^+$) in plasma water; | mmol/L |
| $c_{pw,Na3}Cit$ | Estimated or measured or known pre-dialysis concentration of total citrate in plasma water; | mmol/L |
| $c_{pw,HCO3}$ | Estimated or measured pre-dialysis concentration of bicarbonate anions ($HCO_3^-$) in plasma water; | mL/min |
| $c_{pw,artHCO3}$ | Estimated or measured pre-dialysis concentration of bicarbonate anions ($HCO_3^-$) in blood from patient; | mmol/L |
| $c_{pw,artK}$ | Estimated or measured pre-dialysis concentration of potassium ions ($K^+$) in blood from patient; | mmol/L |
| $c_{pw,artAc}$ | Estimated or measured pre-dialysis concentration of acetate anions ($CH_3COO^-$) in blood from patient; | mmol/L |
| $c_{pw,artNa3}Cit$ | Estimated or measured or known pre-dialysis concentration of total citrate in blood from patient; | mmol/L |
| $K_u$ | Filtration unit clearance for urea; | mL/min |
| $K_{b,Cit}$ | Filtration unit clearance for citrate; | mL/min |
| $K_m A$ | Modified mass transfer coefficient; | mL/min |
| $K_0 A$ | Urea mass transfer coefficient of filtration unit (e.g. average of normally used dialyzers); | mL/min |
| $K_0 A_{Cit}$ | Citrate mass transfer coefficient of filtration unit; | mL/min |
| Pe | Peclet number; | dimensionless |
| $\alpha$ | Donnan effect corrective factor; | Dimensionless |
| $\alpha_{bi}$ | Donnan effect corrective factor in HF/HDF pre-dilution mode; | Dimensionless |
| $\kappa_{di}$ | Conductivity of the dialysis fluid upstream of the filtration unit; | mS/cm |
| $\kappa_{do}$ | Conductivity of the dialysis fluid downstream of the filtration unit (dialysate); | mS/cm |
| D | Dialysance of the filtration unit; | mL/min |
| $\kappa_{p,1}$ | Plasma conductivity first estimate; | mS/cm |
| $K_{0,di}$ | Dialysis fluid conductivity at the filtration unit inlet for a pure electrolyte solution; | mS/cm |
| $\kappa_{0,do}$ | Dialysate conductivity at the filtration unit outlet for a pure electrolyte solution; | mS/cm |
| $f_{bw}$ | Apparent blood water fraction, i.e., the part of whole blood that appears as pure water for urea; | Dimensionless |
| $f_{pw}$ | Plasma water fraction, i.e., the part of plasma that is pure water; | Dimensionless |
| $f_{cw}$ | Cell water fraction; | dimensionless |
| Hct | Red cell fraction of blood; | dimensionless |
| $f_i$ | Dialyzable blood water fraction for substance i of the dialyzer blood (i = $Na^+$, $HCO_3^-$, $K^+$, $Ac^-$, $Cit^3$); | dimensionless |
| $f_{HCO3}$ | Dialyzable blood water fraction for bicarbonate ions ($HCO_3$) of the dialyzer blood; | dimensionless |
| $f_K$ | Dialyzable blood water fraction for potassium ions ($K^+$) of the dialyzer blood; | dimensionless |
| $f_{Ac}$ | Dialyzable blood water fraction for acetate ions ($Ac^-$) of the dialyzer blood; | dimensionless |
| $f_{Cit}$ | Dialyzable blood water fraction for substance citrate ions ($Cit^{3-}$) of the dialyzer blood; | dimensionless |
| $\gamma_{cw,u}$ | Plasma water fraction; | dimensionless |
| $c_{p,tp}$ | Total plasma protein concentration in blood leaving patient; | g/L |
| $c_{pi,tp}$ | Total plasma protein concentration in blood entering dialyzer; | g/L |
| $c_{di,Na,isocond}$ | Isoconductive sodium concentration; | mmol/L |
| c | Concentrations; | mmol/L |
| $c_{p,Na}$ | Plasma sodium concentration; | mmol/L |
| $c_{pw,Na}$ | Concentration of sodium ($Na^+$) in plasma water; | mmol/L |
| $c_{pw}$ | Plasma water concentration; | mmol/L |
| $c_d$ | Dialysis fluid concentration; | mmol/L |
| $c_{di,Na}$ | Dialysis fluid concentration of sodium at the filtration unit inlet; | mmol/L |
| $c_{do,Na}$ | Dialysis fluid concentration of sodium at the filtration unit outlet; | mmol/L |
| T | Total treatment time; | min |
| WL | Wight loss; | Kg |

The Donnan factor adjusts for electrical effects on ions assuring electroneutrality to be kept over the membrane. For estimating the Donnan factor reference is made to Trans Am Soc Artif Intern Organs, 1983; 29; 684-7, "Sodium Fluxes during hemodialysis", Lauer A., Belledonne M., Saccaggi A., Glabman S., Bosch J.

In order to implement a method for estimation of plasma sodium during hemodialysis a model of ion transport in the filtration unit has been developed. Indeed, if the blood values of some electrolytes are known or estimated, the plasma sodium may be calculated from the conductivity measurements by a simple filtration unit model.

According to the developed method a term, named $c_{di,Na,isocond}$, is the dialysis fluid isoconductive sodium concentration and a term, named $C_{di,Na,offset}$, is a term to obtain the plasma sodium concentration.

For two dialysis fluid separate settings (e.g. different conductivity and/or concentration of at least one solute), denoted with indices 1 and 2, the first term can be calculated by the expression:

$$c_{di,Na,isocond} = \frac{\square_{di,Na,1} * (K_{do,2} - K_{di,2}) - c_{di,Na,2} * (K_{do,1} - K_{di,1})}{(K_{do,2} - K_{di,2}) - (K_{do,1} - K_{di,1})} \quad (I)$$

For HD, HDF post-dilution and HF post-dilution treatment mode, the term to obtain the plasma sodium concentration can be calculated through the expression:

$$c_{di,Na,offset} = \quad (II)$$
$$-\frac{1}{M_{K,NaCl}} * \Big[(M_{K,NaHCO_3} - M_{K,NaCl}) * (\alpha^{-1} * c_{pw,HCO_3} - c_{d,HCO_3}) +$$
$$M_{K,KCl} * (\alpha * c_{pw,K} - c_{d,K}) +$$
$$(M_{K,NaAc} - M_{K,NaCl}) * (\alpha^{-1} * c_{pw,Ac} - c_{d,Ac}) + \frac{Q_{do}}{K_u} * (k_{rest})\Big]$$

The plasma sodium relates to plasma water as:

$$c_{p,Na} = f_{pw} * c_{pw,Na} \quad (III)$$

where the plasma water fraction ($f_{pw}$) is usually about 0.93:

$$f_{pw} \approx 0.93$$

In view of the above calculations, it derives that:

$$c_{p,Na} = \frac{f_{pw}}{\alpha} * (c_{di,Na,isocond} + c_{di,Na,offset}) \quad (IV)$$

For HDF pre-dilution and HF pre-dilution treatment mode, the term to obtain the plasma sodium concentration can be calculated through the expression:

$$c_{di,Na,offset} = -\frac{1}{M_{K,NaCl}} \cdot \Big[(M_{K,NaHCO_3} - M_{K,NaCl}) \cdot \quad (V)$$
$$\left(\frac{1}{\alpha_{bi}} \cdot \frac{Q_b \cdot f_{HCO_3} \cdot c_{pw,art_{HCO_3}} + Q_{inf} \cdot c_{d_{HCO_3}}}{Q_b \cdot f_{HCO_3} + Q_{inf}} - c_{d,HCO_3}\right) +$$
$$M_{K,KCl} \cdot \left(\alpha_{bi} \cdot \frac{Q_b \cdot f_K \cdot c_{pw,art_K} + Q_{inf} \cdot c_{d_K}}{Q_b \cdot f_K + Q_{inf}} - c_{d,K}\right) +$$
$$(M_{K,NaAc} - M_{K,NaCl}) \cdot$$
$$\left(\frac{1}{\alpha_{bi}} \cdot \frac{Q_b \cdot f_{Ac} \cdot c_{pw,art_{Ac}} + Q_{inf} \cdot c_{d_{Ac}}}{Q_b \cdot f_{Ac} + Q_{inf}} - c_{d,Ac}\right) + \frac{K_{b_{Cit}}}{K_u} \cdot$$
$$(M_{K,Na_3Cit} - 3M_{K,NaCl}) \cdot (0.167\alpha_{bi}^{-3} + 0.125\alpha_{bi}^{-2} + 0.706\alpha_{bi}^{-1}) \cdot$$
$$\frac{Q_b \cdot f_{Cit} \cdot c_{pw,art_{Na_3Cit}} + Q_{inf} \cdot c_{d_{Na_3Cit}}}{Q_b \cdot f_{Na_3Cit} + Q_{inf}} -$$
$$c_{d,Na_3Cit}\Big) + \frac{Q_{do}}{K_u} * (k_{rest})\Big]$$

In HF treatment mode, the clearance being equal to the dialyzer outlet flow, i.e. $K_u = Q_{do}$.

Solution Proposal

The technical solution here described is applicable to HD, HDF, and HF treatment modes, particularly making use of concentrates with acetate and/or citrate.

The above described model is extremely useful in determining the blood parameter of interest. Various steps of the proposed method which will be described below are intended to be performed by the control unit 12 of the extracorporeal blood treatment device 1, even if not explicitly stated.

In particular a treatment session is started, preferably, but not necessarily, as a double needle hemodialysis treatment.

The user shall input the prescription values through the user interface 22. For example the set values for total weight loss WL and total treatment time T are provided, as well as the blood flow rate $Q_b$ and the fresh dialysis flow rate $Q_{di}$. If required also infusion rate, $Q_{inf}$ or total accumulated infusion volume, $V_{inf}$, is provided.

Other parameters may be entered through the user interface, such as bag type, sodium user limits, etc.

The operator has to further input the 'bicarbonate' set before starting the treatment.

The control unit 12 receives from the prescription or, alternatively, calculates either the initial dialysis liquid conductivity or the initial concentration of at least one solute, e.g. sodium, in the dialysis liquid.

In this respect it is worth to note that, in the following detailed description, reference is made to regulating means controlling concentration of an ionic substance, in detail sodium concentration, in the preparation of the dialysis fluid so as to obtain a desired conductivity of the dialysis fluid.

However, regulating means directly regulating the overall dialysis fluid conductivity is also included in the spirit of the present description or, alternatively, regulating means modifying the concentration of a different ionic substance is included in the present description, too.

The hemodialysis or hemodiafiltration or hemofiltration treatment is thereafter started.

The isoconductive sodium concentration is provided to the control unit 12. In more detail, the isoconductive sodium concentration may be calculated according expression I.

Alternatively, an isoconductive sodium concentration related parameter may be provided to the control unit 12; the isoconductive sodium concentration related parameter may be the plasma conductivity. Indeed the isoconductive sodium concentration is correlated to the plasma conductivity; it is possible to derive, in a manner known to the person skilled in the art, the isoconductive sodium concentration knowing the plasma conductivity and vice versa; of course the composition of the dialysis fluid should be known. Indeed, the conductivity of a solution may be calculated as a sum of terms; each term represents a salt contained in the solution and each term is constructed as the product of the molar conductivity and concentration of the salt. The concentration of sodium may be calculated from conductivity from the same relation. In such a case the plasma conductivity (subsequently used to obtain the isoconductive sodium concentration) may be calculated by conventional methods, for example according to anyone of the methods according to EP547025, U.S. Pat. No. 5,100,554, EP658352, EP920877 or EP1108438.

As mentioned, in case the isoconductive sodium concentration (or the isoconductive sodium concentration related parameter) is not known, different methods may be used to determine the relevant parameter.

In a HD treatment mode, to calculate the isoconductive sodium concentration (or the isoconductive sodium concentration related parameter) the conductivity upstream and downstream the filtration unit is measured for the flowing dialysis fluid passing through the filtration unit.

During the same HD treatment mode, then an adjusted dialysis fluid having a different concentration of a solute, e.g. sodium, is prepared and the conductivity upstream and downstream the filtration unit is measured again for the adjusted dialysis fluid; for example the two dialysis fluids may differ of about 10 mmol/L.

In other terms, the basic principle of the above described monitoring systems is the continuous measurement of the outlet dialysate conductivity when the inlet dialysate conductivity is changed for example 1 mS/cm during, for example, two (or more) minutes.

Alternatively, the control unit 12 directly receives as an input the isoconductive sodium concentration or plasma conductivity. This is valid for all HD/HDF/HF treatment modes. For example, the physician or the nurse may receive a lab analysis and may provide the datum to the machine through the user interface of the dialysis monitor; the control unit 12 is programmed for storing in a memory 46 the isoconductive sodium concentration or the plasma conductivity to be used for the following dialysis fluid parameter regulation.

In addition (for all HD/HDF/HF treatment modes), the isoconductive sodium concentration or the plasma conductivity may be estimated using different formulas, not explicitly requiring two dialysis fluids at different sodium concentrations. This is particularly the case for HDF and HF treatment modes. Also for HD treatment mode the following method may be adopted.

For example, according to a further embodiment (implementable for HD/HDF and HF treatment modes), the control unit 12 is programmed to calculate the initial plasma conductivity based on the sum of at least the initial conductivity of the dialysate plus a difference between inlet and outlet conductivity at the filtration unit, or dialyzer, weighted by a factor of the dialysate flow rate. In more detail the difference between inlet and outlet conductivity at the filtration unit is weighted by a factor of the blood flow rate in the blood lines too.

Specifically, according to this further embodiment, the control unit 12 is configured to calculate the plasma conductivity using the following formula:

$$K'_{p,1} = K_{0,do} + \frac{Q_{do}}{Q_{Bset}}(K_{0,do} - K_{0,di}) \qquad (VI)$$

The significance of the denotations above is given in the Glossary.

It is worth to underline that during the above described calculation of the initial plasma conductivity (formula (VI)), in HD and HDF treatment modes, the dialysis fluid circulates through the secondary chamber 4 maintaining the dialysis fluid parameter value substantially constant.

In HF and HDF treatment modes, the dialysis/infusion fluid circulates through the infusion line 39, again maintaining the dialysis fluid parameter value substantially constant.

In an additional embodiment, the control unit 12 is programmed to calculate the initial plasma conductivity based on the sum of at least the initial conductivity of the fresh dialysis fluid plus a difference between inlet and outlet conductivity at the filtration unit weighted by a factor of the dialysate flow rate. In more detail the difference between inlet and outlet conductivity at the filtration unit, or dialyzer, is weighted by a factor of the filtration unit clearance too.

Specifically, according to the additional embodiment, the control unit 12 is configured to calculate the plasma conductivity using the following formula:

$$K''_{p,1} = K_{0,di} + \frac{Q_{do}}{K_u}(K_{0,do} - K_{0,di}) \qquad (VII)$$

The significance of the denotations and constants above is given in the Glossary.

It is worth to underline that during the above described calculation of the initial plasma conductivity (formula (VII)), in HD and HDF treatment modes, the dialysis fluid circulates through the secondary chamber 4 maintaining the dialysis fluid parameter value substantially constant.

In HF and HDF treatment modes, the dialysis/infusion fluid circulates through the infusion line 39, again maintaining the dialysis fluid parameter value substantially constant.

Of course, both formulas (VI) and (VII) for estimation of plasma conductivity may be iteratively applied, meaning that the newly calculated estimate of PC ($k_{p,1}$) is imposed to the dialysis fluid and a new estimate again calculated after taking measures of the conductivity at the inlet and outlet of the filter as soon as stable conditions are reached.

Estimation of Dialyzer Clearance

Since the filtration unit (dialyzer) clearance $K_u$ isn't known (see e.g. above formula (VII) requiring clearance $K_u$), it is necessary to estimate it. For the purpose of the estimation, it is assumed that all ions have the same dialyzer clearance, which is equal to the urea clearance.

In HDF treatments it is of fundamental importance to distinguish between the dialyzer clearance, which is related to the transport across the membrane, and the treatment (patient) clearance which describes the removal of a substance from the patient. The patient clearance has clinical interest, whereas for the purpose of calculating the initial set point the interest is in the dialyzer properties. Thus, when clearance is referred to in this document, unless otherwise stated, it is the filtration unit/dialyzer clearance.

In the calculation of clearance, the ultrafiltration flow through the membrane must be taken into account. The total ultrafiltration flow $Q_u$ is the sum of the weight loss flow rate $Q_{wl}$ and the infusion flow $Q_{inf}$:

$$Q_u = Q_{wl} + Q_{inf} \qquad (VIII)$$

In HD treatment mode, the infusion flow $Q_{inf}$ is zero.

In general, the infusion flow $Q_{inf}$ is the sum of the pre-infusion flow rate (i.e. the fluid infused in the blood circuit 17 upstream the filtration unit 2) and the post-infusion flow rate (i.e. the fluid infused in the blood circuit 17 downstream the filtration unit 2).

The dialyzer inlet fluid flow is:

$$Q_{di} = Q_d - Q_{inf} \qquad (IX)$$

where $Q_d$ is the total dialysis fluid flow rate, i.e. the total flow rate of dialysis fluid which is prepared by the preparation device 9 and which is then split (if appropriate) into a fluid flow ($Q_{di}$) to the filtration unit and a fluid flow ($Q_{inf}$) to be infused in the blood circuit.

In HF treatment mode, the dialyzer inlet fluid flow $Q_{di}$ is zero, since $Q_d = Q_{inf}$.

The dialyzer outlet fluid flow $Q_{do}$ can be calculated as:

$$Q_{do} = Q_{di} + Q_u \qquad (X)$$

The $K_u$ can be calculated with the following equations:

$$K_u = Q_{bwi} \cdot \frac{1 - \frac{Q_{bwo}}{Q_{bwi}} \cdot \psi}{1 - \frac{Q_{bwo}}{Q_{do}} \cdot \psi} \qquad (XI)$$

where $$\psi = \frac{Q_{do}}{Q_{di}} \cdot \left(\frac{Q_{bwo} \cdot Q_{do}}{Q_{bwi} \cdot Q_{di}}\right)^{\frac{K_m A}{Q_u}} \qquad (XII)$$

$k_m A$ is the modified mass transfer coefficient:

$$k_m A = \frac{Pe}{e^{Pe} - 1} * k_0 A \qquad \text{(XIII)}$$

and $k_0 A$ is the mass transfer coefficient of the dialyzer.

$k_0 A$ may be derived having information about the dialyzer used, e.g. the apparatus may receive the data from the user or by reading the specific component identification data. Alternatively the control unit 12 may assume a standard dialyzer with, e.g. a $k_0 A = 1100$ ml/min as a fixed value. In this latter case, the error in calculated K will be within ±10% for all the commonly used dialyzers.

Pe is the so called Peclet number which is defined as $$Pe = \frac{Q_u}{k_0 A} \qquad \text{(XIV)}$$

$Q_{bwi}$ is the dialyzer inlet blood water flow, which in HD and HDF post-dilution can be calculated as:

$$Q_{bwi} = f_{bw} Q_b \qquad \text{(XV)}$$

Vice versa, in HDF pre-dilution, the dialyzer inlet blood water flow must include the infusion flow:

$$Q_{bwi} = f_{bw} Q_b + Q_{inf} \qquad \text{(XVI)}$$

In this equation, $Q_b$ is the real (arterial) blood flow rate and $f_{bw}$ is the dialyzable blood water fraction, which can be calculated with the equation:

$$f_{bw} = f_{cw} \cdot \gamma_{cw,u} \cdot Hct + f_{pw} \cdot (1 - Hct) \qquad \text{(XVII)}$$

wherein the used symbols meaning is clarified in the glossary section.

With the reference values stated above, the dialyzable blood water fraction $f_{bw}$ for urea will be, e.g. 0.89 at normal conditions for hemodialysis.

The dialyzer outlet blood water flow can be calculated from $$Q_{bwo} = Q_{bwi0} - Q_u \qquad \text{(XVIII)}$$

Estimation of Dialyzer Clearance—HF Treatment

In the HF treatment mode, the clearance calculation is simple, since the clearance is equal to the dialyzer outlet flow:

$$K_u = Q_{do} = Q_u = Q_{inf} + O_{wl} \qquad \text{(XIX)}$$

Since by definition, $Q_{di} = 0$ in HF.

Estimation of Citrate Clearance

For citrate, the free ion $Cit^{3-}$ does not dominate over its complexes and ion pairs. There are substantial parts of $CaCit^-$, $MgCit^-$ and $NaCit^{2-}$ together with some $HCit^{2-}$ depending on pH in blood plasma and dialysis solutions.

We approximate that the individual clearance values are close to a single value denoted $K_{b_{Cit}}$.

This clearance is calculated for the actual flow rates using a mass transfer coefficient value of $k_0 A_{Cit} = 0.212 \cdot k_0 A$ into the $K_u$ formulas (4), (5), (6).

Estimation of the Plasma Water Fraction

HD and HDF/HF Post-Dilution

The plasma water fraction depends on the total plasma protein concentration $c_{p,tp}$ and can be estimated as:

$$f_{pw} = 1 - 0.00107 \cdot c_{p,tp} \qquad \text{(XX)}$$

where $c_{p,tp}$ is the plasma protein concentration. With a normal plasma protein concentration $c_{p,tp} = 70$ g/L, the plasma water fraction is $f_{pw} = 0.925$.

HDF/HF Pre-Dilution

In HDF and HF pre-dilution mode, the dilution of the blood and the corresponding reduction of the total protein concentration must be taken into account to calculate the plasma water fraction for the blood in the dialyzer.

This is done with the following equations:

$$c_{pi,tp} = \frac{Q_b * (1 - Hct) * c_{p,tp}}{Q_b * (1 - Hct) + Q_{inf}} \qquad \text{(XXI)}$$

$$f_{pw} = 1 - 0.00107 \cdot c_{pi,tp} \qquad \text{(XXII)}$$

the used symbols meaning is clarified in the glossary section.

Estimation of the Donnan Factor $\alpha$

HD and HDF/HF Post-Dilution

The transport of charged permeable substances over the dialyzer membrane is affected by the charged plasma proteins. The effect is quantified by a Donnan factor $\alpha$.

If the plasma protein concentration $c_{p,tp}$ is known, the Donnan factor $\alpha$ for a single charged cation can be estimated with the equation:

$$\alpha = 1.004 e^{-0.0008 * c_{p,tp}} \qquad \text{(XXIII)}$$

With a normal plasma total protein concentration $c_{p,tp} = 70$ g/L, the Donnan factor is $\alpha = 0.95$ at conditions typical for hemodialysis.

HDF/HF Pre-Dilution

In HDF and HF pre-dilution mode, the dilution of the blood and the corresponding reduction of the total protein concentration must be taken into account when calculating the Donnan factor for the blood in the dialyzer.

This is done with the following equations:

$$c_{pi,tp} = \frac{Q_b * (1 - Hct) * c_{p,tp}}{Q_b * (1 - Hct) + Q_{inf}} \qquad \text{(XXIV)}$$

$$\alpha_{bi} = 1.004 * e^{-0.0008 * c_{pi,tp}} \qquad \text{(XXV)}$$

wherein the used symbols meaning is clarified in the glossary section.

Estimation of Sodium Concentration in Blood (Second Blood Parameter)

As previously mentioned, according to an innovative aspect, the control unit 12 receives a value of a parameter. The parameter may be the isoconductive sodium concentration or the isoconductive sodium concentration related parameter.

As mentioned, the control unit 12 is configured for calculating the value of a second parameter of the blood.

The second parameter is chosen between a concentration of a substance in the blood and a concentration-related parameter of a substance in the blood.

Depending on the specific need, the sodium content (or the content of a different electrolyte) in the blood may be determined.

The step of calculating the value of the second parameter of the blood is performed as a function of a main contribution term based on/function of the isoconductive sodium concentration and as a function of an offset contribution term, i.e. a term which takes into account the transport driving gradient of certain specific substances.

The main contribution term may affect (may contribute to) the sodium concentration for at least 80% of the same parameter value (and in particular for at least 90% of the parameter value), i.e. the general value of the sodium concentration in plasma mainly depend on isoconductive sodium concentration.

In more detail, the offset contribution term may contribute to the sodium concentration in blood for less than 20% (or even less than 15%) of the same parameter value (and in particular for less than 10% of the parameter value).

The calculation is a weighted algebraic sum of at least the main contribution term ($C_{di,Na,isocond}$) and the offset contribution term ($C_{di,Na,offset}$) according to the following general formula:

$$c_{p,Na} = \frac{f_{pw}}{\alpha} * (c_{di,Na,isocond} + c_{di,Na,offset}) \quad (XXVI)$$

In order to estimate the blood sodium content, i.e. $c_{p,Na}$, an offset factor $C_{di,Na,offset}$, needs to be applied to the isoconductive sodium concentration, i.e. $C_{di,Na,isocond}$.

The main contribution term ($C_{di,Na,isocond}$) is a concentration value which, if used as a dialysis fluid concentration of sodium would run an isoconductive dialysis; we define 'isoconductive dialysis', as a dialysis treatment where the conductivity of the dialysis fluid does not change pre- to post-filtration unit 2, $\kappa_{di}=\kappa_{do}$.

As clear from formula (XXVI) the concentration of plasma sodium is a weighted sum of $C_{di,Na,isocond}$ and $C_{di,Na,offset}$. In particular the algebraic sum of the two terms is multiplied by a factor $f_{pw}/\alpha$, i.e. the plasma water fraction divided by the Donnan factor.

Though not essential since a calculation may be made based on conductivities too, the main contribution term and the offset contribution term are dimensionally concentrations of a substance (e.g. sodium) in a fluid.

The Applicant has understood that certain specific substances present in the dialysis fluid, namely bicarbonate, potassium, acetate, and citrate have a major effect which should be taken into account when it is desired to estimate the blood sodium content from a measure of isoconductive sodium concentration. Of course other substances play a role, such as lactate, magnesium, and calcium.

Furthermore, the difference in concentration between same substances in the blood and in the dialysis fluid influences, as well, the mentioned estimation.

Given the above, the Applicant also realized that in calculating the offset contribution term, certain parameters having a weight in determining the overload of sodium are known and depends on the machine dressing (e.g. used concentrates) or on the prescription for the patient (e.g. dialysate flow rate). Other parameters depend on the patient undergoing the treatment and therefore may be either directly measured (e.g. lab analysis) or estimated (e.g. based on large population numbers or patient history).

The offset contribution term assumes, in all or almost all prevailing dialysis settings, a negative value, i.e. reduces the main contribution term, this latter being a concentration value which if used as concentration of sodium in the dialysis fluid would allow an isoconductive treatment.

Indeed, the main contribution term takes into consideration the effect of all the ions in causing the isoconductive sodium concentration; the offset contribution term modify this value to determine the sodium (or another substance) concentration only.

In more detail, the control unit is configured to calculate the offset contribution term based on a concentration of at least a substance in the dialysis fluid chosen in the group including bicarbonate, potassium, acetate, lactate, and citrate; in particular calculation is made as a function of the concentration of at least two of said substances, and in further detail as a function of the concentration of bicarbonate, potassium, acetate, and/or citrate, and lactate in the dialysis fluid.

As mentioned, the control unit is configured to calculate the offset contribution term as a function of the weighted difference in concentration of at least one of the above cited substances in the dialysis fluid and the same substances in the blood plasma.

In case of HDF pre-dilution and HF pre-dilution treatment modes, the estimated plasma water concentration of the specific substance (i), e.g. sodium, bicarbonate, potassium, acetate, and citrate, is replaced with the corresponding diluted blood concentration to take into consideration dilution due to pre-infusion.

Additionally, the control unit calculates the offset contribution term as a function of the molar conductivities of at least a substance in the dialysis fluid; in detail the substance may be chosen in the group including acids or salts of bicarbonate, chloride, acetate, citrate, phosphate, and sulphate, wherein the salt is formed with sodium, potassium, calcium, and magnesium.

In more detail, the calculations take into account the molar conductivities of at least two of said substances, specifically of at least three and particularly of sodium bicarbonate ($NaHCO_3$), sodium chloride (NaCl), sodium acetate ($NaCH_3COO$), trisodium citrate ($Na_3C_6H_5O_7$), and potassium chloride (KCl).

Again, the offset contribution term is a function of the differences between two molar conductivities, a first molar conductivity of a substance chosen in the group including sodium bicarbonate ($NaHCO_3$), sodium acetate ($NaCH_3COO$), trisodium citrate ($Na_3C_6H_5O_7$), and potassium chloride (KCl), and a molar conductivity of sodium chloride (NaCl).

Alternatively, the offset contribution term is a function of the differences between two molar conductivities, a first molar conductivity of a substance chosen in the group including sodium bicarbonate ($NaHCO_3$), trisodium citrate ($Na_3C_6H_5O_7$), and potassium chloride (KCl), and a molar conductivity of sodium chloride (NaCl).

The control unit is also configured to calculate the offset contribution term as a function of an estimated plasma water concentration of at least a substance chosen in the group including bicarbonate, potassium, acetate, lactate, and citrate; in particular the calculation is made based on the estimated plasma water concentration of at least two, three or four of said substances; in one specific example of the present description the offset contribution term is a function of the estimated plasma water concentration of bicarbonate, potassium, and acetate. In another specific example citrate too is considered.

In HD, HDF post-dilution and HF post-dilution, the estimated plasma water concentration of bicarbonate, potassium, citrate, and acetate is the mean pre-dialysis values of the corresponding substance for large patient populations. As previously mentioned, the estimated plasma water concentration of bicarbonate, potassium, and acetate may alternatively be based on other statistical prepared values, or historical values for the specific patient, or direct measurements made before the treatment.

In respect to HDF pre-dilution and HF pre-dilution, the estimated plasma water concentration in blood entering the dialyzer takes into account the dilution of the blood due to the infusion of substitution fluid upstream the dialyzer.

The estimated plasma water concentration in HDF pre-dilution and HF pre-dilution modes is a function of the blood flow rate $Q_b$ and of the infusion flow rate $Q_{inf}$. Furthermore, it is also function of the dialyzable blood water fraction for the selected substance (calculated based on hematocrit—Hct—and cell water fraction) and of the plasma water concentration in blood from patient (i.e. upstream the pre-dilution infusion point); the estimated plasma water concentration is also function of the infusion fluid concentration of the same substance.

Note that, in the specific formula, the estimated plasma water concentration may alternatively be adjusted by a respective (preferably, but not necessarily, fixed) adjusting factor. Numerical values can be e.g. 0.95 ($\alpha$) or 1.05 ($\alpha^{-1}$), but other values may be used (generally depending on the protein content and charge of the ions).

More in detail, the adjusting factor is function of the charged plasma proteins, and particularly of the Donnan factor. In HD, HDF post-dilution and HF post-dilution modes, the adjusting factor is the Donnan factor $\alpha$ or its reciprocal $\alpha^{-1}$. In HDF pre-dilution and HF pre-dilution modes, the adjusting factor should take into consideration the reduction of total protein concentration due to pre-dilution infusion. Therefore, the adjusting factor is in this latter case function of the diluted protein concentration affected by blood flow $Q_b$, infusion flow $Q_{inf}$ and red cell fraction of blood Hct (see e.g. equation (XXV)).

The offset contribution term is an algebraic sum of a plurality of components, a first component being function of the difference, in particular a weighted difference, in concentration of at least a substance in the dialysis fluid and the same substance in the blood plasma, the second component being function of the difference, in particular a weighted difference, in concentration of at least a second substance in the dialysis fluid and the same second substance in the blood plasma, the third component being function of the difference, in particular a weighted difference, in concentration of at least a third substance in the dialysis fluid and the same third substance in the blood plasma.

The substance may be chosen in the group including bicarbonate anions ($HCO_3^-$), acetate anions ($CH_3COO^-$), citrate anions ($C_6H_5O_7^{3-}$), and potassium ions ($K^+$), but additionally also lactate.

Again, in case of HDF pre-dilution and HF pre-dilution treatment modes, the estimated plasma water concentration of the specific substance (i), e.g. sodium, bicarbonate, potassium, acetate, and citrate, is replaced with the corresponding diluted blood concentration to take into consideration dilution due to pre-infusion. Therefore, the difference above mentioned is a difference between a diluted blood concentration and the concentration in the dialysis fluid of the same substance.

The above general consideration is reflected in specific and non-limiting implementing formulas which allow, when the isoconductive sodium concentration is known, to determine the precise sodium concentration in the blood.

Of course, different formulas including one or more of the general principles/substances above stated may be alternatively used.

As previously mentioned, in order to estimate the sodium content in blood, i.e. $c_{p,Na}$, an offset factor $C_{di,Na,offset}$ needs to be applied to the calculated isoconductive sodium concentration:

$$c_{p,Na} = \frac{f_{pw}}{\alpha} * (c_{di,Na,isocond} + c_{di,Na,offset}) \quad \text{(XXVII)}$$

HD Treatment Mode
In case of HD treatment mode:

$$c_{di,Na,offset} = -\frac{1}{M_{\kappa,NaCl}} * [ \quad \text{(XXVIII)}$$
$$(M_{\kappa,NaHCO_3} - M_{\kappa,NaCl}) * (\alpha^{-1} * c_{pw,HCO_3} - c_{d,HCO_3}) +$$
$$M_{\kappa,KCl} * (\alpha * c_{pw,K} - c_{d,K}) +$$
$$(M_{\kappa,NaAc} - M_{\kappa,NaCl}) * (\alpha^{-1} * c_{pw,Ac} - c_{d,Ac})]$$

Alternatively, in case also the effect of other substances is to be taken into account, the offset factor may be calculated with a similar formula which includes a further term in the algebraic sum.

The further term is a fourth component in the sum depending on at least a ratio between one flow rate, in particular the dialysate flow rate at the outlet of the secondary chamber 4, and an efficiency parameter of the filtration unit 2, in particular a clearance of the filtration unit 2, optionally the urea clearance.

In this case the formula would read:

$$c_{di,Na,offset} = -\frac{1}{M_{\kappa,NaCl}} * \quad \text{(XXIX)}$$
$$\left[ (M_{\kappa,NaHCO_3} - M_{\kappa,NaCl}) * (\alpha^{-1} * c_{pw,HCO_3} - c_{d,HCO_3}) + \right.$$
$$M_{\kappa,KCl} * (\alpha * c_{pw,K} - c_{d,K}) +$$
$$\left. (M_{\kappa,NaAc} - M_{\kappa,NaCl}) * (\alpha^{-1} * c_{pw,Ac} - c_{d,Ac}) + \frac{Q_{do}}{K_u} * (k_{rest}) \right]$$

Factor $\kappa$ (namely, $\kappa_{rest}$) defines the effect on the conductivity due to other components in the dialysis fluid different from the components already treated and included in the respective formula. Thus, the effect of salts containing calcium, magnesium, lactate, phosphate, and sulphate may have upon the conductivity. The effect created by these components is most often small, and does not vary considerably between the dialysis treatments.

In case citrate is taken into consideration, the formula would read:

$$c_{di,Na,offset} = \quad \text{(XXX)}$$
$$-\frac{1}{M_{\kappa,NaCl}} * \left[ (M_{\kappa,NaHCO_3} - M_{\kappa,NaCl}) * (\alpha^{-1} * c_{pw,HCO_3} - c_{d,HCO_3}) + \right.$$
$$M_{\kappa,KCl} * (\alpha * c_{pw,K} - c_{d,K}) + (M_{\kappa,NaAc} - M_{\kappa,NaCl}) *$$
$$(\alpha^{-1} * c_{pw,Ac} - c_{d,Ac}) + \frac{K_{bCit}}{K_u} (M_{\kappa_{Na_3Cit}} - 3 M_{\kappa_{NaCl}})$$
$$((0.167\alpha^{-3} + 0.125\alpha^{-2} + 0.706\alpha^{-1}) * c_{pw,Na_3Cit} -$$
$$\left. c_{d,Na_3Cit}) + + \frac{Q_{do}}{K_u} * (k_{rest}) \right]$$

$K_{b_{Cit}}$ is the approximated clearance value for citrate. This clearance may be calculated for the actual flow rates using a mass transfer value of $K_0 A_{Cit} = 0.212 * K_0 A_{Urea}$ in the corresponding $K_u$ formula.

HDF Post-Dilution Treatment Mode

In case of HDF treatment mode post-dilution, the same equations (XXVIII-XXX) as for HD treatment mode applies, but with the clearance $K_u$ calculated for the HDF treatment case with the substitution flow rate taken into account (see equations (XI-XVI)).

HDF Pre-Dilution Treatment Mode

The equations for HDF pre-dilution are similar to HDF post, but we must take into account the dilution of the blood before it enters the dialyzer.

The dilution of the plasma water concentration of substance I in pre-dilution mode is described by equation (XXXI) here-below reported for ease of comprehension:

$$c_{pw,bi} = \frac{Q_b \cdot f_i \cdot c_{pw,art} + Q_{inf} \cdot c_{inf}}{Q_b \cdot f_i + Q_{inf}} \quad (XXXI)$$

The offset factor is calculated as follows:

$$c_{di,Na,offset} = -\frac{1}{M_{K,NaCl}} \cdot \left[ (M_{K,NaHCO_3} - M_{K,NaCl}) \cdot \right.$$

$$\left( \frac{1}{\alpha_{bi}} \cdot \frac{Q_b \cdot f_{HCO_3} \cdot c_{pw,art_{HCO_3}} + Q_{inf} \cdot c_{d_{HCO_3}}}{Q_b \cdot f_{HBO_3} + Q_{inf}} - c_{d,HCO_3} \right) +$$

$$M_{K,KCl} \cdot \left( \alpha_{bi} \cdot \frac{Q_b \cdot f_K \cdot c_{pw,art_K} + Q_{inf} \cdot c_{d_K}}{Q_b \cdot f_K + Q_{inf}} - c_{d,K} \right) +$$

$$(M_{K,NaAc} - M_{K,NaCl}) \cdot$$

$$\left( \frac{1}{\alpha_{bi}} \cdot \frac{Q_b \cdot f_{Ac} \cdot c_{pw,art_{Ac}} + Q_{inf} \cdot c_{d_{Ac}}}{Q_b \cdot f_{Ac} + Q_{inf}} - c_{d,Ac} \right) +$$

$$\frac{K_{b_{Cit}}}{K_u} \cdot (M_{K,Na_3Cit} - 3M_{K,NaCl}) \cdot$$

$$(0.167\alpha_{bi}^{-3} + 0.125\alpha_{bi}^{-2} + 0.706\alpha_{bi}^{-1}) \cdot$$

$$\left. \frac{Q_b \cdot f_{Cit} \cdot c_{pw,art_{Na_3Cit}} + Q_{inf} \cdot c_{d_{Na_3Cit}}}{Q_b \cdot f_{Na_3Cit} + Q_{inf}} - c_{\square,Na_3Cit} \right)\right] \quad (XXXII)$$

In case also the effect of other substances is to be taken into account, the offset factor may be calculated with a similar formula which includes a further term in the algebraic sum.

The further term is a fourth component in the sum depending on at least a ratio between one flow rate, in particular the dialysate flow rate at the outlet of the secondary chamber 4, and an efficiency parameter of the filtration unit 2, in particular a clearance of the filtration unit 2, optionally the urea clearance $K_u$. Of course, dilution of the blood due to pre-infusion of substitution fluid should be taken into account.

HF Pre-Dilution Treatment Mode

The equations for HF pre-dilution are the same equations as HDF pre-dilution, but with the filtration unit clearance equal to dialysate flow rate at filtration unit outlet, i.e. $K_u = Q_{do}$.

HF Post-Dilution Treatment Mode

The equations for HF post-dilution are the same equations as HD, but with the filtration unit clearance equal to dialysate flow rate at filtration unit outlet, i.e. $K_u = Q_{do}$.

Once the sodium concentration in blood is calculated, the control unit may drive the regulating means 10 for regulating the conductivity or the concentration of the substance in the fresh dialysis fluid and sets the third parameter value for the dialysis fluid in the dialysis fluid supply line 8 at a calculated set point based on the estimated blood sodium content. The third parameter may be the sodium concentration in the dialysis fluid or the conductivity or the same dialysis fluid.

Of course, the estimated blood sodium content may also be used to create a sodium profile in time to be applied to the specific patient in order to control the sodium balance throughout the dialysis treatment.

The invention claimed is:

1. An apparatus for extracorporeal blood treatment comprising:
   a filtration unit having a primary chamber and a secondary chamber separated by a semi-permeable membrane;
   a blood circuit including a blood withdrawal line connected to an inlet of the primary chamber and a blood return line connected to an outlet of the primary chamber, the blood withdrawal line and the blood return line being configured for connection to a patient cardiovascular system;
   a dialysis supply line including at least one infusion line connected to said blood circuit;
   a dialysis effluent line connected to an outlet of the secondary chamber;
   a preparation device configured to prepare dialysis fluid, the preparation device in fluid communication with the dialysis supply line;
   a regulator configured to regulate a composition of the dialysis fluid; and
   a control unit in operable communication with the regulator, the control unit configured to run at least a hemofiltration (HF) treatment or a hemodiafiltration (HDF) treatment, each of said treatments including an infusion of substitution fluid through said infusion line, the control unit being programmed for receiving a value of a first parameter representative of an isoconductive dialysis, the first parameter being chosen from a group consisting of a concentration of at least one substance, a concentration-related parameter of at least one substance, a conductivity or a conductivity-related parameter, wherein said control unit is configured for:
   calculating the value of a second parameter of the blood, said second parameter being chosen from a group consisting of a concentration of at least one substance in the blood and a concentration-related parameter of at least one substance in the blood, wherein the step of calculating the value of the second parameter is performed as a function of a main contribution term based on the first parameter and as a function of an offset contribution term based on a concentration of at least one substance in the dialysis fluid chosen from a group consisting of bicarbonate, potassium, acetate, lactate, citrate, magnesium, calcium, sulphate, and phosphate;
   storing said second parameter value in a memory connected to the control unit;
   setting a third parameter value for the dialysis fluid in the dialysis supply line at a set point based on the second parameter, said third parameter of the dialysis fluid being a conductivity of the dialysis fluid or a concentration of at least one substance in the dialysis fluid; and
   causing the regulator to regulate the conductivity of the dialysis fluid or the concentration of at least one substance in the dialysis fluid at the set point.

2. Apparatus according to claim 1, wherein the control unit is configured to calculate the offset contribution term based on the concentration of two or more substances in the dialysis fluid chosen from a group consisting of bicarbonate, potassium, acetate, lactate, citrate, magnesium, calcium, sulphate, and phosphate.

3. Apparatus according to claim 1, wherein the control unit is configured to calculate the offset contribution term as a function of a weighted difference in concentration of at least one substance in the dialysis fluid and the same substance in the plasma, said substance being chosen from a group consisting of bicarbonate, potassium, acetate, lactate, and citrate.

4. Apparatus according to claim 1, wherein the control unit is configured to calculate the offset contribution term as a function of the weighted difference in concentration in the dialysis fluid and in the plasma of at least three substances chosen from a group consisting of bicarbonate, potassium, acetate, and citrate.

5. Apparatus according to claim 1, wherein the first parameter is the isoconductive sodium concentration or isoconductive sodium concentration-related parameter and the second parameter is the concentration of at least one substance in the blood, said substance being sodium.

6. Apparatus according to claim 1, wherein the main contribution term is dimensionally a concentration of a substance in a fluid, wherein the main contribution term is a concentration value which, if used as a dialysis fluid concentration of sodium, would perform an isoconductive dialysis.

7. Apparatus according to claim 1, wherein the main contribution term affects the second parameter for at least 80% of the second parameter value, the offset contribution term contributes to the second parameter for less than 20% of the second parameter value, and wherein the sub-step of calculating the second parameter value as a function of the main contribution term and the offset contribution term is a sub-step of calculating an algebraic sum of at least the main contribution term and the offset contribution term.

8. Apparatus according to claim 1, further including a preparation device for preparing a dialysis fluid connected to said supply line and comprising a regulator for regulating the composition of the dialysis fluid, the regulator being connected to the control unit.

9. Apparatus according to claim 8, wherein said control unit is configured for determining a profile in time for a third parameter value for the dialysis fluid in the dialysis supply line, said third parameter of the dialysis fluid being at least one chosen from a group consisting of a conductivity of the dialysis fluid, a conductivity-related parameter of the dialysis fluid, a concentration of at least one substance in the dialysis fluid and a concentration-related parameter of at least one substance in the dialysis fluid, and wherein the control unit drives the regulator for regulating the conductivity or the concentration of at least one substance in the dialysis fluid, the profile in time for the third parameter being based on the second parameter.

10. Apparatus according to claim 1, wherein the control unit is configured to calculate the offset contribution term as a function of the molar conductivities of at least one substance in the dialysis fluid chosen from a group consisting of sodium bicarbonate ($NaHCO_3$), sodium chloride (NaCl), sodium acetate ($NaCH_3COO$), potassium chloride (KCl), sodium lactate ($NaC_3H_5O_3$), and trisodium citrate ($Na_3C_6H_5O_7$).

11. Apparatus according to claim 1, wherein the control unit is configured to calculate the offset contribution term as a function of the molar conductivities of at least three of said substances chosen from a group consisting of sodium bicarbonate ($NaHCO_3$), sodium chloride (NaCl), sodium acetate ($NaCH_3COO$), trisodium citrate ($Na_3C_6H_5O_7$), and potassium chloride (KCl).

12. Apparatus according to claim 1, wherein the control unit is configured to calculate the offset contribution term as a function of a difference between (i) a first molar conductivity of a substance chosen from a group consisting of sodium bicarbonate ($NaHCO_3$), sodium acetate ($NaCH_3COO$), trisodium citrate ($Na_3C_6H_5O_7$), sodium lactate ($NaC_3H_5O_3$), and potassium chloride (KCl), and (ii) a second molar conductivity of sodium chloride (NaCl).

13. Apparatus according to claim 1, wherein the control unit is configured to calculate the offset contribution term as a function of an estimated or measured plasma water concentration of at least two substances chosen from a group consisting of bicarbonate, potassium, acetate, lactate, and citrate, and wherein for HDF pre-dilution treatment and HF pre-dilution treatment, said estimated or measured plasma water concentration is a diluted plasma concentration, the diluted plasma concentration being a function of the blood flow rate and of the infusion flow rate.

14. Apparatus according to claim 13, wherein the control unit is configured to calculate the offset contribution term as an algebraic sum of at least two components, a first component being a function of the weighted difference in concentration of at least one substance in the dialysis fluid and the same substance in the blood plasma, a second component being a function of the weighted difference in concentration of at least one second substance in the dialysis fluid and the same second substance in the blood plasma, wherein said first and second substances are chosen from a group consisting of bicarbonate anions ($HCO_3^-$), acetate anions ($CH_3COO^-$), citrate anions ($C_6H_5O_7^{3-}$), and potassium ions ($K^+$), and wherein, for HDF pre-dilution treatment and HF pre-dilution treatment, said estimated or measured plasma water concentration of a substance is a diluted plasma concentration, the diluted plasma concentration being a function of the blood flow rate and of the infusion flow rate.

15. Apparatus according to claim 14, wherein the diluted plasma concentration is a function of a dialyzable blood water fraction for said substance and the plasma water concentration in blood from patient, and of a concentration of said substance in the infused fluid.

16. Apparatus according to claim 14, wherein the control unit is configured to calculate the isoconductive sodium concentration as a function of a conductivity of the dialysis liquid upstream of the filtration unit, a conductivity of the dialysis liquid downstream of the filtration unit, the dialysis fluid flow rate at the inlet of the secondary chamber, and an efficiency parameter of the filtration unit or the blood flow rate.

17. Apparatus according to claim 16, wherein said control unit is configured to determine the isoconductive sodium concentration from at least two conductivity values determined respectively upstream and downstream of said filtration unit in at least two successively prepared dialysates with different concentrations.

18. Apparatus according to claim 1, wherein the control unit is configured to calculate the offset contribution term as an algebraic sum of at least two components, a first component being a function of a concentration of at least one substance in the dialysis fluid and/or in the blood plasma, a second component being a function of a concentration of at least one second substance in the dialysis fluid and/or in the blood plasma, wherein said first and second substances are chosen from a group consisting of bicarbonate anions ($HCO_3^-$), acetate anions ($CH_3COO^-$), citrate anions ($C_6H_5O_7^{3-}$), and potassium ions ($K^+$).

19. Apparatus according to claim 1, wherein the offset contribution term is based on a weighted difference in concentration of at least one substance in the dialysis fluid and the same substance in the plasma, said substance being chosen in the group including bicarbonate, potassium, acetate, lactate, and citrate.

20. Apparatus according to claim 1, wherein the control unit is configured to calculate the offset contribution term as a function of a difference between a first molar conductivity of a substance chosen in the group including sodium bicarbonate, sodium acetate, trisodium citrate, sodium lactate, potassium chloride, and a molar conductivity of sodium chloride.

21. Apparatus according to claim 1, wherein the regulator is a pump.

22. An apparatus for extracorporeal blood treatment comprising:
 a filtration unit having a primary chamber and a secondary chamber separated by a semi-permeable membrane;
 a blood circuit including a blood withdrawal line connected to an inlet of the primary chamber and a blood return line connected to an outlet of the primary chamber, said blood withdrawal line and blood return line being configured for connection to a patient cardiovascular system;
 a dialysis supply line including at least one infusion line connected to said blood circuit;
 a dialysis effluent line connected to an outlet of the secondary chamber;
 a preparation device configured to prepare dialysis fluid, the preparation device in fluid communication with the dialysis supply line;
 a regulator configured to regulate a composition of the dialysis fluid; and
 a control unit in communication with the regulator, the control unit configured to run at least a hemofiltration (HF) treatment or a hemodiafiltration (HDF) treatment, each of said treatments including an infusion of substitution fluid through said infusion line, the control unit being programmed for receiving a value of a first parameter for an isoconductive dialysis, the first parameter being chosen from a group consisting of a concentration of at least one substance and a conductivity, wherein said control unit is configured for:
 calculating the value of a second parameter of the blood, said second parameter being a concentration of at least one substance in the blood, wherein the step of calculating the value of the second parameter is performed as a function of a main contribution term based on the first parameter and as a function of an offset contribution term based on a concentration of at least one substance in the dialysis fluid chosen from a group consisting of bicarbonate, potassium, acetate, lactate, citrate, magnesium, calcium, sulphate, and phosphate,
 storing the second parameter value in a memory connected to the control unit,
 setting a third parameter value for the dialysis fluid in the dialysis supply line at a set point based on the second parameter, said third parameter of the dialysis fluid being a conductivity of the dialysis fluid or a concentration of at least one substance in the dialysis fluid, and
 causing the regulator to regulate the conductivity of the dialysis fluid or the concentration of at least one substance in the dialysis fluid at the set point,
 wherein the main contribution term affects the second parameter for at least 80% of the second parameter value, the offset contribution term contributes to the second parameter for less than 20% of the second parameter value, and wherein the sub-step of calculating the second parameter value as a function of the main contribution term and the offset contribution term is a sub-step of calculating an algebraic sum of at least the main contribution term and the offset contribution term, and
 wherein the control unit is configured to calculate the offset contribution term as a function of a difference in concentration of at least one substance in the dialysis fluid and the same substance in the plasma, said substance being chosen from a group consisting of bicarbonate, potassium, acetate, lactate, and citrate.

23. Apparatus according to claim 22, wherein the regulator is a pump.

* * * * *